United States Patent
Saito et al.

(10) Patent No.: US 8,299,185 B2
(45) Date of Patent: Oct. 30, 2012

(54) CURABLE CAGE-TYPE SILICONE COPOLYMER AND PROCESS FOR PRODUCTION THEREOF AND CURABLE RESIN COMPOSITION COMPRISING CURABLE CAGE-TYPE SILICONE COPOLYMER AND CURED PRODUCT THEREOF

(75) Inventors: Takashi Saito, Kisarazu (JP); Mitsuhiro Koike, Kisarazu (JP); Yuko Murakami, Kisarazu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 292 days.

(21) Appl. No.: 12/809,556

(22) PCT Filed: Dec. 25, 2008

(86) PCT No.: PCT/JP2008/073528
§ 371 (c)(1),
(2), (4) Date: Jun. 18, 2010

(87) PCT Pub. No.: WO2009/084562
PCT Pub. Date: Jul. 9, 2009

(65) Prior Publication Data
US 2010/0280190 A1 Nov. 4, 2010

(30) Foreign Application Priority Data

Dec. 27, 2007 (JP) ................................. 2007-337059
Mar. 24, 2008 (JP) ................................. 2008-076618

(51) Int. Cl.
*C08G 77/20* (2006.01)
*C08G 77/38* (2006.01)
*C08F 283/12* (2006.01)
*C08L 83/07* (2006.01)
*C08L 83/10* (2006.01)

(52) U.S. Cl. ......................................... 525/477; 528/32
(58) Field of Classification Search .................... 525/477
See application file for complete search history.

(56) References Cited

U.S. PATENT DOCUMENTS

| 5,412,053 | A | * | 5/1995 | Lichtenhan et al. | 528/9 |
| 5,484,867 | A | * | 1/1996 | Lichtenhan et al. | 528/9 |
| 5,589,562 | A | * | 12/1996 | Lichtenhan et al. | 528/9 |
| 6,252,030 | B1 | * | 6/2001 | Zank et al. | 528/31 |
| 7,141,692 | B2 | * | 11/2006 | Allen et al. | 556/460 |
| 7,198,639 | B2 | * | 4/2007 | Lai et al. | 623/6.11 |
| 7,345,125 | B2 | * | 3/2008 | Isozaki et al. | 526/279 |
| 7,373,060 | B2 | * | 5/2008 | Satake et al. | 385/123 |
| 7,410,914 | B2 | * | 8/2008 | Kuehnle et al. | 438/780 |
| 7,514,519 | B2 | * | 4/2009 | Ootake et al. | 528/31 |
| 2006/0100410 | A1 | * | 5/2006 | Ootake et al. | 528/33 |
| 2006/0116499 | A1 | * | 6/2006 | Ootake et al. | 528/9 |
| 2006/0194068 | A1 | * | 8/2006 | Katoh et al. | 428/447 |
| 2006/0204192 | A1 | * | 9/2006 | Satake et al. | 385/123 |
| 2008/0064803 | A1 | * | 3/2008 | Soucek et al. | 524/440 |

FOREIGN PATENT DOCUMENTS

| JP | 2004-123698 A | | 4/2004 |
| JP | 2005-290352 A | | 10/2005 |
| SU | 1523245 A | * | 11/1989 |
| WO | WO-02/094839 A1 | | 11/2002 |
| WO | WO-03/024870 A1 | | 3/2003 |
| WO | WO-2007/119477 A1 | | 10/2007 |

OTHER PUBLICATIONS

Machine Translation of WO 2007119477 obtained from JPO.*
Feher et al. J Am Chem Soc vol. 111, No. 5 1989.*
Mantz et al. Chem. Mater. 1996, 8, 1250-1259.*
Feher and Newman. J. Am. Chem. Soc., vol. 112, No. 5, 1990.*
International Search Report for the Application No. PCT/JP2008/073528 mailed Mar. 17, 2009.
Wright, Michael et al., "Synthesis and Thermal Curing of Aryl-Ethynyl-Terminated coPOSS Imide Oligomers: New Inorganic/Organic Hybrid Resins", Chemistry of Materials, 2003, vol. 15, No. 1, pp. 264-268.
Lichtenhan, Joseph et al., "Silsesquioxane-Siloxane Copolymers from Polyhedral Silsequioxanes", Macromolecules, 1993, vol. 26, No. 8, pp. 2141-2142.
Baney, Ronald et al., "Silsequiexanes", Chemical Reviews, 1995, vol. 95, No. 5, pp. 1409-1430.
Feher, Frank et al., "Facile Syntheses of New Incompletely Condensed Polyhedral Oligosilsesquioxanes: [(c—$C_5H_9$)$_7Si_7O_9(OH)_3$], [(c—$C_7H_{13}$)$_7Si_7O_9(OH)_3$], and [(c—$C_7H_{13}$)$_6Si_8O_7(OH)_4$]", Organometallics, 1991, vol. 10, No. 7, pp. 2526-2528.

* cited by examiner

Primary Examiner — Randy Gulakowski
Assistant Examiner — Mike M Dollinger
(74) Attorney, Agent, or Firm — Cheng Law Group, PLLC

(57) ABSTRACT

Disclosed is a cage-type copolymer in which a cage structure is incorporated in its main chain. Also disclosed is a curable resin composition comprising the said copolymer. Specifically disclosed is a curable cage-type silicone copolymer with a constituent unit represented by general formula (1) $Y—[Z—(O_{1/2}—R^2{}_2SiO_{1/2})_a—(R^1SiO_{3/2})_n—(O_{1/2})_b]—Z—Y$: wherein $R^1$ and $R^2$ each is a vinyl group, an alkyl group, a phenyl group, a (meth)acryloyl group, an allyl group, or an oxirane ring-containing group, Z is a divalent group represented by the following general formula (2) wherein $R^3$ is a hydrogen atom, a vinyl group, an alkyl group, a phenyl group, a (meth)acryloyl group, an allyl group, or an oxirane ring-containing group, and Y is any one of the groups represented by the following general formula (3) $[(R^4O)R^2{}_2SiO_{1/2}]_a—[R^1{}_2SiO_{3/2}]_n—[O_{1/2}]—$, general formula (4) $[R^4O_{1/2}]_b—[R^1SiO_{3/2}]_n—[O_{1/2}—R^2{}_2SiO_{1/2}]—$, general formula (5) $(R^4O_{1/2})—$, and general formula (6) $(R^2{}_3SiO_{1/2})—$ wherein $R^4$ is a hydrogen atom, a methyl group, or an ethyl group.

10 Claims, No Drawings

CURABLE CAGE-TYPE SILICONE COPOLYMER AND PROCESS FOR PRODUCTION THEREOF AND CURABLE RESIN COMPOSITION COMPRISING CURABLE CAGE-TYPE SILICONE COPOLYMER AND CURED PRODUCT THEREOF

FIELD OF TECHNOLOGY

This invention relates to a curable cage-type silicone copolymer, a process for producing the said curable cage-type silicone copolymer, a curable resin composition comprising the said curable cage-type silicone copolymer, and a cured product of the said curable resin composition. Specifically, this invention relates to a curable cage-type silicone copolymer, a process for producing the said curable cage-type silicone copolymer using a cage-type silsesquioxane compound containing an alkoxyl or silanol group, and a curable resin composition comprising the said curable cage-type silicone copolymer.

BACKGROUND TECHNOLOGY

A large number of studies have been conducted on polymers formed from cage-type silsesquioxanes or their derivatives. These polymers are expected to have excellent properties in respect to heat resistance, weather resistance, optical characteristics, dimensional stability, and the like. For example, a process for producing a copolymer that consists of incompletely condensed silsesquioxanes (of an incomplete octagonal structure wherein the space is not closed due to cleavage of at least one bond) joined together by siloxane bonds is disclosed in the non-patent document 1. The process comprises introducing an amine or the like to a silsesquioxane of an incomplete cage structure through the aid of an organometallic compound and then crosslinking the resulting product with an aromatic imide or phenyl ether. Further, a process for producing a copolymer through the reaction of silanol groups possessed by a silsesquioxane of an incomplete cage structure with an aminosilane or the like is disclosed in the non-patent document 2.

In particular, electronic materials and optical materials are in need of improvements in heat resistance, durability, and moldability, and of further improvements in transparency and weather resistance depending upon the parts in which the materials are used. However, the conventional silsesquioxane copolymers have an indistinct structure and lack stability or cage-type silsesquioxanes undergo gelation when they are grafted to the main chain as they form a crosslinking point. Therefore, it is difficult to obtain a structure fully furnished with the aforementioned characteristics. For this reason, there is a demand for copolymers of excellent moldability in which a cage-type silsesquioxane of excellent heat resistance, weather resistance, and optical characteristics constitutes the main chain and the position of bond is clearly defined. However, there have been known few examples of copolymers in which a cage-type silsesquioxane is incorporated in the main chain.

Processes of copolymerization for producing a variety of copolymers are reported in the following patent documents 1 and 2; the processes comprise hydrolyzing a silane compound containing a trifunctional hydrolyzable group in an organic solvent in the presence of an alkali metal hydroxide to synthesize a silsesquioxane of an incomplete cage structure containing Si—ONa as a reactive group and then reacting this silsesquioxane of an incomplete cage structure with a chlorosilane that has a functional group capable of serving the purpose. To the knowledge of the inventors of this invention, however, no reports have been published other than the aforementioned ones. Moreover, a matter of concern here is that the aforementioned processes might restrict the side chains possessed by the cage-type silsesquioxane and provide poor heat resistance due to lack of curability. That is, materials of excellent properties are difficult to produce freely with good reproducibility by these methods.

By the way, studies on cage-type siloxanes or derivatives thereof are conducted actively (for example, refer to the non-patent document 3). Hydrolyzable group-containing derivatives of cage-type siloxanes are particularly useful as the reactivity of a hydrolyzable group can be utilized to derive new siloxane compounds. For example, Feher and co-workers report that they obtained a cage-type siloxane containing a silanol group by hydrolyzing a chlorosilane followed by aging (refer to the non-patent document 4).

However, the process of Feher and co-workers is problematical in that the synthesis requires a long time, the amount of by-products is large, and the yield of the target product is low. That is, a process for synthesizing a cage-type siloxane compound containing a silanol group that starts from a hydrolyzable group-containing monosilane faces the following problem; both hydrolysis and condensation reactions need to be controlled and, in addition, the molecular weight changes with passage of time as the condensation reaction proceeds between silanol groups being formed as the silanol group itself is extremely unstable. Therefore, it is substantially impossible to control the introduction of the silanol group freely. Recently, as the aforementioned patent documents 1 and 2 and the following patent document 3 propose, a silane compound containing a trifunctional hydrolyzable group is hydrolyzed in an organic solvent in the presence of an alkali metal hydroxide to yield a precursor in which Si—ONa is introduced as a reactive group in place of a silanol group (Si—OH) and the precursor is used for the production of silsesquioxane derivatives.

Patent document 1: WO2002/094839 pamphlet
Patent document 2: WO2003/024870 pamphlet
Patent document 3: JP2004-123698 A
Non-patent document 1: Chem. Mater., 2003, 15, 264-268
Non-patent document 2: Macromolecules, 1993, 26, 2141-2142
Non-patent document 3: Chem. Rev., 1995, 95, 1409
Non-patent document 4: Organometallics, 1991, 10, 2526

DISCLOSURE OF THE INVENTION

Problems to be Solved by the Invention

As explained above, if it were possible to control the molecular weight freely in the production of a copolymer and design the material to serve the purpose, the freedom in molding of electronic materials and optical materials would increase further. However, examples of the synthesis of copolymers in which a cage structure is incorporated in the main chain are few and concrete characteristics of such copolymers are not clarified sufficiently. Further, it has been difficult to produce cage-type siloxanes containing a controlled amount of silanol groups because of the instability of the silanol group. Still further, no report has been published on a process for producing a cage-type siloxane in which hydrolyzable alkoxyl groups are introduced freely.

Accordingly, it is an object of this invention to provide a cage-type siloxane compound containing an alkoxyl group or silanol group in which the molecular structure is controlled and the alkoxyl group or silanol group is incorporated freely and to provide further a copolymer in which a cage structure is incorporated in the main chain using the said cage-type siloxane compound containing an alkoxyl group or silanol group and a curable resin composition comprising the said copolymer.

Means to Solve the Problems

The inventors of this invention have conducted intensive studies to solve the aforementioned problems and found that a copolymer in which a cage structure is incorporated in the main chain can be obtained by condensation of a cage-type silsesquioxane compound containing an alkoxyl group or silanol group under the specified reaction conditions. The inventors further found that a curable resin composition comprising the said copolymer can yield a cured product of excellent transparency and heat resistance and completed this invention.

Thus, this invention relates to a curable cage-type silicone copolymer characterized by having a constituent unit represented by the following general formula (1):

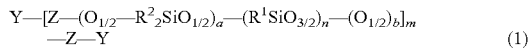
(1)

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$, n denotes a number of 8-14, and m denotes a number of 1-2,000; Z is a divalent group represented by the following general formula (2)

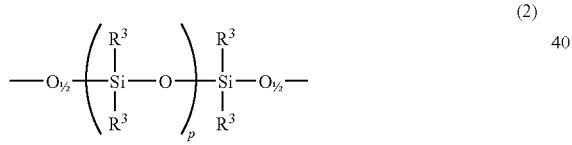
(2)

wherein $R^3$ is a hydrogen atom, a vinyl group, an alkyl group, a phenyl group, a (meth)acryloyl group, an allyl group, or an oxirane ring-containing group; the substituents selected for $R^3$ may be identical with or different from one another; p denotes a number of 0-30; and Y is a monovalent group selected from the following general formulas (3) to (6)

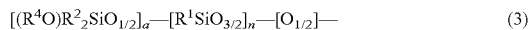
(3)

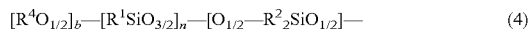
(4)

(5)

(6)

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from one another; $R^4$ is selected from a hydrogen atom, a methyl group, and an ethyl group; a and b each is a number of 0-3 and n denotes a number of 8-14.

Further, this invention relates to a process for producing a curable cage-type silicone copolymer characterized by having a constituent unit represented by the following general formula (1):

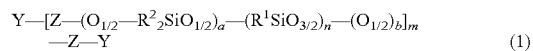
(1)

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$ and n denotes a number of 8-14; in the case where n is an odd number, a and b are a combination of an even number and an odd number including 0; in the case where n is an even number, a and b are a combination of even numbers including 0; m denotes a number of 1-2,000; Z is a divalent group represented by the following general formula (2)

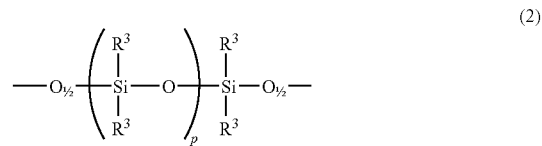
(2)

wherein $R^3$ is a hydrogen atom, a vinyl group, an alkyl group, a phenyl group, a (meth)acryloyl group, an allyl group, or an oxirane ring-containing group, the substituents selected for $R^3$ may be identical with or different from one another, and p denotes a number of 0-30; and Y is a monovalent group selected from the following general formulas (3) to (6)

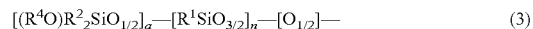
(3)

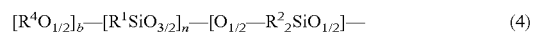
(4)

(5)

(6)

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from one another; $R^4$ is selected from a hydrogen atom, a methyl group, and an ethyl group; a and b each is a number of 0-3 and n denotes a number of 8-14; in the case where n is an odd number, a and b each is independently 0 or 2; in the case where n is an even number, a and b each is independently 1 or 3: the said process comprising condensing a cage-type siloxane compound containing an alkoxyl group or silanol group represented by the following general formula (7)

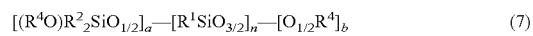
(7)

(wherein $R^1$ and $R^2$ each is selected from a vinyl group, an alkyl group, a phenyl group, a (meth)acryloyl group, an allyl group, and an oxirane ring-containing group; $R^4$ is selected from a hydrogen atom, a methyl group, and an ethyl group; the substituents selected for $R^1$, $R^2$, or $R^4$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$; further, n is an integer of 8-14; in the case where n is an odd number, a and b are a combination of an even number and an odd number including 0; in the case where n is an even number, a and b are a combination of even numbers including 0) with a compound represented by the following general formula (8)

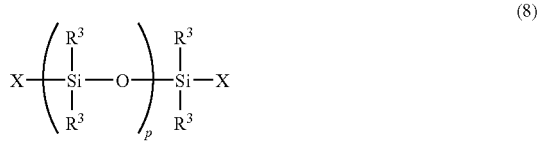

(8)

(wherein $R^3$ is a hydrogen atom, a vinyl group, an alkyl group, a phenyl group, a (meth)acryloyl group, an allyl group, or an oxirane ring-containing group; the substituents selected for $R^3$ may be identical with or different from one another; X is a hydroxyl group, a hydrogen atom, a chlorine atom, or an alkoxyl group; the substituents selected for X may be identical with or different from one another; further, p denotes a number of 0-30), and then condensing the said condensation reaction product with a compound represented by the following general formula (9)

$$R^2_3Si\text{---}X \quad (9)$$

(wherein $R^2$ is a hydrogen atom, a vinyl group, an alkyl group, a phenyl group, a (meth)acryloyl group, an allyl group, or an oxirane ring-containing group, the substituents selected for $R^2$ may be identical with or different from one another, and X is a hydroxyl group, a hydrogen atom, a chlorine atom, or an alkoxyl group).

Further, this invention relates to a cage-type siloxane compound containing an alkoxyl group that is obtained by the addition reaction of a cage-type siloxane compound represented by the following general formula (19)

$$[R^1SiO_{3/2}]_n \quad (19)$$

(wherein $R^1$ is selected from a vinyl group, an alkyl group, a phenyl group, a (meth)acryloyl group, an allyl group, and an oxirane ring-containing group, the substituents selected for $R^1$ may be identical with or different from one another, and n is an integer of 8-14) with a dialkoxysilane represented by the following general formula (20)

$$R^2_2Si(OR^5)_2 \quad (20)$$

(wherein $R^2$ is selected from a vinyl group, an alkyl group, a phenyl group, a (meth)acryloyl group, an allyl group, and an oxirane ring-containing group, $R^5$ is selected from a methyl group and an ethyl group, and the substituents selected for $R^2$ or $R^5$ may be identical with or different from one another) in a non-polar solvent in the presence of a basic catalyst.

Further, this invention relates to a cage-type siloxane compound containing a silanol group that is obtained by the hydrolysis of the aforementioned cage-type siloxane compound containing an alkoxyl group in the presence of an acid catalyst or a basic catalyst and is represented by the following general formula (7-2):

$$[(HO)R^2_2SiO_{1/2}]_a\text{---}[R^1SiO_{3/2}]_n\text{---}[O_{1/2}H]_b \quad (7-2)$$

wherein $R^1$ and $R^2$ each is selected from a vinyl group, an alkyl group, a phenyl group, a (meth)acryloyl group, an allyl group, and an oxirane ring-containing group; the substituents selected for $R^1$ or $R^2$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$; further, n is an integer of 8-14.

Further, this invention relates to a process for producing a cage-type siloxane compound containing an alkoxyl group which comprises mixing a cage-type siloxane compound represented by the following general formula (19)

$$[R^1SiO_{3/2}]_n \quad (19)$$

(wherein $R^1$ is selected from a vinyl group, an alkyl group, a phenyl group, a (meth)acryloyl group, an allyl group, and an oxirane ring-containing group, the substituents selected for $R^1$ may be identical with or different from one another, and n is an integer of 8-14) and a dialkoxysilane represented by the following general formula (20)

$$R^2_2Si(OR^5)_2 \quad (20)$$

(wherein $R^2$ is selected from a vinyl group, an alkyl group, a phenyl group, a (meth)acryloyl group, an allyl group, and an oxirane ring-containing group, $R^5$ is selected from a methyl group and an ethyl group, and the substituents selected for $R^2$ or $R^5$ may be identical with or different from one another) at a molar ratio $[R^1Si_{3/2}]_n:R^2_2Si(OR^5)_2$ in the range of 1:0.5 to 1:2 and subjecting the mixture to addition reaction in a non-polar solvent in the presence of a basic catalyst.

Still further, this invention relates to a process for producing a cage-type siloxane compound containing a silanol group which comprises mixing a cage-type siloxane compound represented by the following general formula (19)

$$[R^1SiO_{3/2}]_n \quad (19)$$

(wherein $R^1$ is selected from a vinyl group, an alkyl group, a phenyl group, a (meth)acryloyl group, an allyl group, and an oxirane ring-containing group, the substituents selected for $R^1$ may be identical with or different from one another, and n is an integer of 8-14) and a dialkoxysilane represented by the following general formula (20)

$$R^2_2Si(OR^5)_2 \quad (20)$$

(wherein $R^2$ is selected from a vinyl group, an alkyl group, a phenyl group, a (meth)acryloyl group, an allyl group, and an oxirane ring-containing group, $R^5$ is selected from a methyl group and an ethyl group, and the substituents selected for $R^2$ or $R^5$ may be identical with or different from one another) at a molar ratio $[R^1Si_{3/2}]_n:R^2_2Si(OR^5)_2$ in the range of 1:0.5 to 1:2, subjecting the mixture to addition reaction in a non-polar solvent in the presence of a basic catalyst to yield a cage-type siloxane compound containing an alkoxyl group, and then hydrolyzing the said cage-type siloxane compound containing an alkoxyl group in the presence of an acid catalyst or a basic catalyst.

Of the cage-type siloxane compounds containing an alkoxyl group or silanol group represented by general formula (7) in this invention, those cage-type siloxane compounds containing an alkoxyl group can be represented by the following general formula (7-1):

$$[(R^5O)R^2_2SiO_{1/2}]_a\text{---}[R^1SiO_{3/2}]_n\text{---}[O_{1/2}R^5]_b \quad (7-1)$$

wherein $R^1$ and $R^2$ each is selected from a vinyl group, an alky group, a phenyl group, a (meth)acryloyl group, an allyl group, and an oxirane ring-containing group; $R^5$ is selected from a methyl group and an ethyl group; the substituents selected for $R^1$, $R^2$, or $R^5$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$; further, n is an integer of 8-14.

Examples of the structures of the cage-type siloxane compounds containing an alkoxyl group represented by general formula (7-1) are shown below in structural formulas (10) to (18). Structural formula (10) corresponds to the case where n=8, a=1, and b=1 in general formula (7-1); structural formula (11) corresponds to the case where n=8, a=2, and b=0; structural formula (12) corresponds to the case where n=8, a=0, and b=2; structural formula (13) corresponds to the case where n=9, a=1, and b=2; structural formula (14) corresponds to the case where n=10, a=1, and b=1; structural formula (15) corresponds to the case where n=11, a=1, and b=2; structural formula (16) corresponds to the case where n=12, a=1, and b=1; structural formula (17) corresponds to the case where n=13, a=1, and b=2; and structural formula (18) corresponds to the case where n=14, a=1, and b=1. As there are different combinations of n, a, and b for the cage-type siloxane compounds containing an alkoxyl group, their examples are not limited to those shown above. The groups $R^1$, $R^2$, and $R^5$ in structural formulas (10) to (18) are the same as those in general formula (7-1).

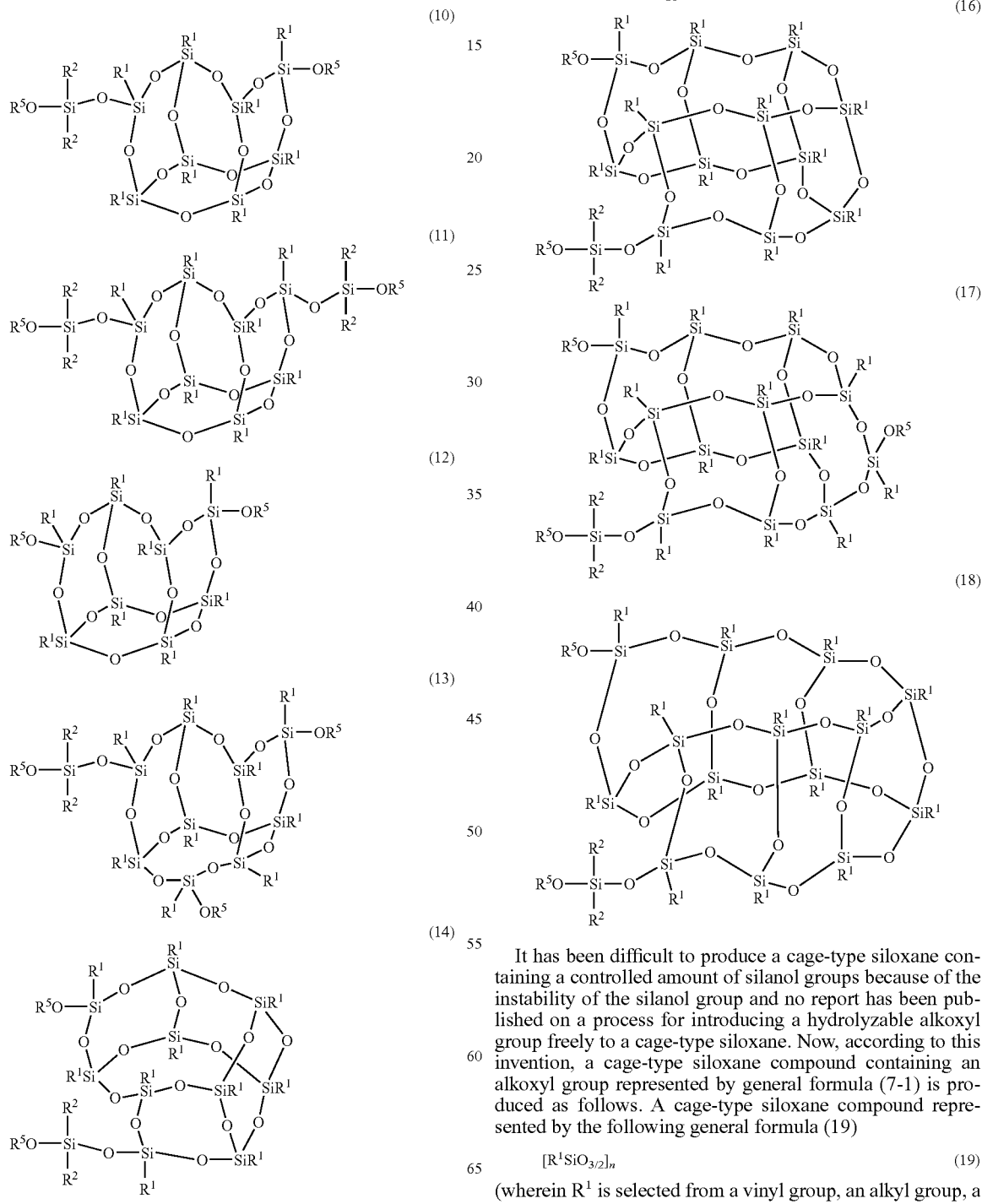

It has been difficult to produce a cage-type siloxane containing a controlled amount of silanol groups because of the instability of the silanol group and no report has been published on a process for introducing a hydrolyzable alkoxyl group freely to a cage-type siloxane. Now, according to this invention, a cage-type siloxane compound containing an alkoxyl group represented by general formula (7-1) is produced as follows. A cage-type siloxane compound represented by the following general formula (19)

(wherein $R^1$ is selected from a vinyl group, an alkyl group, a phenyl group, a (meth)acryloyl group, an allyl group, and an oxirane ring-containing group, the substituents selected for $R^1$ may be identical with or different from one another, and n is an integer of 8-14), obtained by a known method, is added to a dialkoxysilane represented by the following general formula (20)

$$R^2{}_2Si(OR^5)_2 \quad (20)$$

(wherein $R^2$ is selected from a vinyl group, an alkyl group, a phenyl group, a (meth)acryloyl group, an allyl group, and an oxirane ring-containing group, $R^5$ is selected from a methyl group and an ethyl group, and the substituents selected for $R^2$ or $R^5$ may be identical with or different from one another) in a non-polar solvent in the presence of a basic catalyst.

Examples of the cage-type siloxane compounds represented by general formula (19) to be used in this invention are shown below in structural formulas (21) to (24); the structural formulas respectively correspond to the case where n is 8, 10, 12, or 14 in general formula (19). The groups $R^1$ and $R^2$ in structural formulas (21) to (24) are the same as in general formula (7-1).

(21)

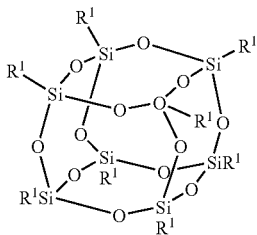

(22)

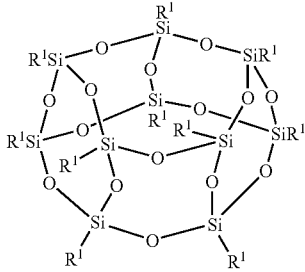

(23)

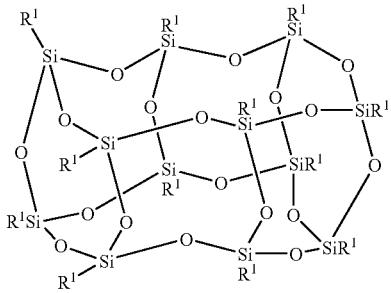

(24)

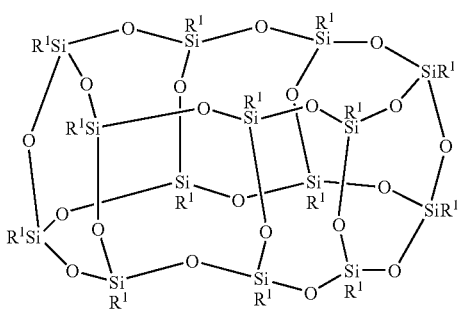

In general formula (19) representing cage-type siloxane compounds, n is an integer of 8-14, preferably 8, 10, or 12, more preferably 8. According to this invention, a cage-type siloxane compound represented by general formula (19) may be used as a mixture with n in the range of 8-14, but it is preferable to use a compound with n of a single number.

Preferable examples of the dialkoxysilanes represented by general formula (20) suitable for use in this invention include dimethyldimethoxysilane, diethyldimethoxysilane, phenylmethyldimethoxysilane, vinylmethyldimethoxysilane, ethyl allyl dimethoxysilane, styrylmethyldimethoxysilane, divinyldimethoxysilane, 3-glycidoxypropylmethyldimethoxysilane, 3-methacryloxypropyldimethoxysilane, 3-acryloxypropyldimethoxysilane, dimethyldiethoxysilane, diethyldiethoxysilane, phenylmethyldiethoxysilane, vinylmethyldiethoxysilane, ethylallyldiethoxysilane, styrylmethyldiethoxysilane, divinyldiethoxysilane, 3-glycidoxypropylmethyldiethoxysilane, 3-methacryloxypropyldiethoxysilane, and 3-acryloxypropyldiethoxysilane.

The addition reaction of a cage-type siloxane compound represented by general formula (19) and a dialkoxysilane represented by general formula (20) is carried out in a non-polar solvent in the presence of a basic catalyst. The non-polar solvent to be used here may be any non-polar solvent that shows no solubility or practically no solubility in water and is preferably a hydrocarbon. A hydrocarbon with a relatively low boiling point such as toluene, benzene, and xylene is suitable and toluene is preferred. The basic catalysts useful for this invention include alkali metal hydroxides such as potassium hydroxide, sodium hydroxide, and cesium hydroxide and quaternary ammonium hydroxides such as tetramethylammonium hydroxide, tetraethylammonium hydroxide, tetrabutylammonium hydroxide, benzyltrimethylammonium hydroxide, and benzyltriethylammonium hydroxide. Of these basic catalysts, the one that is soluble in a non-polar solvent such as a tetraalkylammonium salt is preferable. In particular, tetramethylammonium hydroxide is used more preferably for its high catalytic activity.

The addition reaction of a cage-type siloxane compound represented by general formula (19) and a dialkoxysilane represented by general formula (20) in a non-polar solvent in the presence of a basic catalyst presumably proceeds as follows. First, the siloxane bond in a cage-type siloxane is cleaved by a basic catalyst. Then, the end of the cleaved siloxane bond undergoes an alcohol exchange reaction with the alkoxyl group of a dialkoxysilane to form a siloxane bond with the alkoxyl group (addition reaction) while the ends of the broken siloxane bonds join together intramolecularly or intermolecularly (recombination reaction); the addition reaction and the recombination reaction here occur competitively. Therefore, it is necessary to let the former or addition reaction occur preferentially. As the reaction in this invention is basically an equilibrium reaction, the number average molecular weight $M_n$, yield, and rate of formation of the target cage-type siloxane compound containing an alkoxyl group are naturally decided by the reaction temperature, reaction time, ratio by weight of added raw materials, amount of a basic catalyst, and the like and the reaction is preferably carried out under the conditions to be described below.

The addition reaction of a cage-type siloxane compound represented by general formula (19) and a dialkoxysilane represented by general formula (20) in a non-polar solvent in the presence of a basic catalyst is preferably carried out in an inert atmosphere, for example, in an atmosphere of nitrogen in order to suppress the reaction of the alkoxyl group in general formula (20) with moisture inside the reaction system to form a silanol group or to suppress hydrolytic condensation of the alkoxyl group. The reaction temperature is set below the boiling point of a dialkoxysilane represented by general formula (20), preferably in the range of 70-200° C., more preferably in the range of 80-130° C. When the reaction temperature is too low, the driving force sufficient to advance the addition reaction is not obtained and the reaction does not proceed. When the reaction temperature is too high, there may arise the possibility that some compounds containing a reactive unsaturated functional group such as a vinyl group and a (meth)acryloyl group undergo polymerization by themselves. In a case such as this, it is necessary to control the reaction temperature or add a polymerization inhibitor.

Although the amount of a non-polar solvent to be used is not limited, it is preferably 1 to 5 times that of the weight of a cage-type siloxane compound in consideration of the efficiency of agitation and the kettle efficiency. A dialkoxysilane is preferably added at a rate of 0.5-2.0 moles per 1 mole of a cage-type siloxane compound. It is possible to control the amount of alkoxyl groups in a cage-type siloxane compound containing an alkoxyl group by controlling the amount of a dialkoxysilane to be added. For example, the reaction of 1 mole of a cage-type siloxane compound with 1 mole of a dialkoxylsilane gives a mixture of cage-type siloxane compounds containing two alkoxyl groups in a unit of the cage structure. The said product corresponds to the case where a+b=2 in the following general formula (7-1)

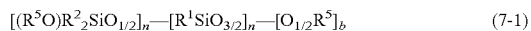

$$[(R^5O)R^2{}_2SiO_{1/2}]_a—[R^1SiO_{3/2}]_n—[O_{1/2}R^5]_b \qquad (7\text{-}1)$$

wherein $R^1$, $R^2$, $R^5$, and n are as defined earlier. In the case where the raw material cage-type siloxane compound is a mixture, the content of the alkoxyl group in the cage structural unit can be controlled by controlling the amount added of a dialkoxysilane on the basis of the average value of n. When the amount added of a dialkoxysilane exceeds the range of 0.5-2.0 moles per 1 mole of a cage-type siloxane compound, more siloxane bonds constituting the cage structure are cleaved and add to alkoxyl groups and, as a result, the cage structure disintegrates. The reaction of 1 mole of a cage-type siloxane compound with 0.5-2.0 moles of a dialkoxysilane yields a cage-type siloxane compound containing an alkoxyl group with a number average molecular weight $M_n$ of 500-2,000 and a molecular weight distribution (weight average molecular weight $M_w$/number average molecular weight $M_n$) of 1.0-2.0.

The basic catalyst is used at a rate of 0.01-0.15 mole, preferably 0.06-1.0 mole, per 1 mole of a cage-type siloxane compound. In the case where a cage-type siloxane compound is a mixture, the catalyst is added at a rate of 0.01-0.15 mole, preferably 0.06-0.1 mole, on the basis of the average value of n.

The cage-type siloxane compound containing an alkoxyl group represented by general formula (7-1) for use in this invention varies with the kind and purity of the cage-type siloxane compound to be used and the amount, kind, and purity of the dialkoxysilane to be added and also with the reaction conditions and the state of the polycondensation product. However, the candidate cage-type siloxane compound containing an alkoxyl group is generally a mixture of a plurality of compounds respectively satisfying the following conditions of general formula (7-1): a and b each is a number of 0-3 and satisfies the relationship $1 \leq a+b \leq 4$ and n denotes an integer of 8-14.

On the other hand, of the cage-type siloxane compounds containing an alkoxyl group or silanol group represented by general formula (7) of this invention, those containing a silanol group can be represented by the following general formula (7-2):

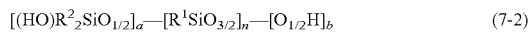

$$[(HO)R^2{}_2SiO_{1/2}]_a—[R^1SiO_{3/2}]_n—[O_{1/2}H]_b \qquad (7\text{-}2)$$

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$; further, n is an integer of 8-14. This compound can be obtained by hydrolyzing a cage-type siloxane compound containing an alkoxyl group represented by the aforementioned general formula (7-1) in the presence of an acid catalyst or a basic catalyst. When a cage-type siloxane compound containing an alkoxyl group is produced by the reaction of 1 mole of a cage-type siloxane compound with 0.5-2.0 moles of a dialkoxysilane, the product cage-type siloxane compound containing a silanol group normally shows a number average molecular weight $W_n$ of 500-2,000 and a molecular weight distribution (weight average molecular weight $M_w$/number average molecular weight $M_n$) of 1.0-2.0.

The structural formulas of cage-type siloxane compounds containing a silanol group correspond basically to the aforementioned structure formulas (10) to (18) in which $R^5$ is replaced by a hydrogen atom: that is, structural formula (10) corresponds to the case where n=8, a=1, and b=1; structural formula (11) corresponds to the case where n=8, a=2, and b=0; structural formula (12) corresponds to the case where n=8, a=0, and b=2; structural formula (13) corresponds to the case where n=9, a=1, and b=2; structural formula (14) corresponds to the case where n=10, a=1, and b=1; structural formula (15) corresponds to the case where n=11, a=1, and b=2; structural formula (16) corresponds to the case where n=12, a=1, and b=1, structural formula (17) corresponds to the case where n=13, a=1, and b=2; and structural formula (18) corresponds to the case where n=14, a=1, and b=1. As there are different combinations of n, a, and b, examples are not limited to those mentioned above. The groups $R^1$ and $R^2$ in structural formulas (10) to (18) are the same as those in general formula (7-1).

A cage-type siloxane compound containing an alkoxy group represented by the aforementioned general formula (7-1) is hydrolyzed to a cage-type siloxane compound containing a silanol group in the presence of an acid catalyst or a basic catalyst. Examples of the acid catalysts include hydrochloric acid, sulfuric acid, acetic acid, formic acid, and trifluromethanesulfonic acid. Examples of the basic catalysts include alkali metal hydroxides such as potassium hydroxide, sodium hydroxide, and cesium hydroxide and quaternary ammonium hydroxides such as tetramethylammonium hydroxide, tetraethylammonium hydroxide, tetrabutylammonium hydroxide, benzyltrimethylammonium hydroxide, and benzyltriethylammonium hydroxide.

Water required for the hydrolysis may be water contained in an acid catalyst or a basic catalyst or it may be added separately. The amount of water is preferably 1-3 moles, more preferably 1-1.5 moles, per 1 mole of alkoxyl group in the raw material cage-type siloxane compound containing an alkoxyl group. When the amount of water is too small, conversion of the alkoxyl group to the silanol group becomes incomplete. When the amount of water is in excess, there may arise the undesirable possibility that cleavage of the siloxane bond occurs.

The acid catalyst or the basic catalyst is preferably added at a rate of 0.1-1.5 moles per 1 mole of alkoxyl group of a cage-type siloxane compound containing an alkoxyl group. Use of an excessive amount of the catalyst cleaves the siloxane bond and disintegrates the cage structure.

The hydrolysis reaction is carried out at a reaction temperature of 0-40° C., preferably 10-30° C. When the reaction temperature is below 0° C., the reaction rate drops, some of the alkoxyl groups remain unchanged, and the reaction consumes a long time. On the other hand, when the reaction temperature is above 40° C., the condensation reaction of the silanol groups proceeds in addition to the hydrolysis reaction and, as a result, polymerization of the hydrolysis product is accelerated. The reaction time is preferably 2 hours or more. When the reaction time is less than 2 hours, the hydrolysis reaction does not proceed sufficiently and the alkoxyl groups remain unchanged.

One or both of a non-polar solvent and a polar solvent, preferably both or a polar solvent alone, may be used in the hydrolysis. The polar solvents include alcohols such as methanol, ethanol, and 2-propanol and other polar solvents. A lower alcohol that is soluble in water and contains 1-6 carbon atoms is preferred and 2-propanol is more preferred. When only a non-polar solvent is used, the reaction system does not become homogeneous and the hydrolysis does not proceed sufficiently. As for the non-polar solvents, those cited earlier as examples in the process for producing a cage-type siloxane compound containing an alkoxyl group may be used.

Upon completion of the hydrolysis reaction, a non-polar solvent such as toluene is added to the reaction solution, the solution is neutralized with a weakly basic or weakly acidic solution depending upon the catalyst used, and water or the reaction solvent containing water is separated. The separation of water or the reaction solvent containing water can be effected by washing the solution with an aqueous sodium chloride solution or the like to remove water and other impurities sufficiently and then drying the solution with a drying agent such as anhydrous magnesium sulfate.

A cage-type siloxane compound containing an alkoxyl group or silanol group represented by the following general formula (7) can be obtained by the process described above:

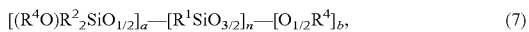

$$[(R^4O)R^2_2SiO_{1/2}]_a - [R^1SiO_{3/2}]_n - [O_{1/2}R^4]_b, \quad (7)$$

wherein $R^1$ and $R^2$ each is selected from a vinyl group, an alkyl group, a phenyl group, a (meth)acryloyl group, an allyl group, and an oxirane ring-containing group; $R^4$ is selected from a hydrogen atom, a methyl group, and an ethyl group; the substituents selected for $R^1$, $R^2$, or $R^4$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$; further, n is an integer of 8-14.

Thereafter, a cage-type siloxane compound containing an alkoxyl group or silanol group represented by general formula (7) is condensed with a compound represented by the following general formula (8)

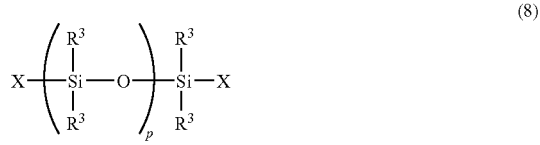

$$(8)$$

(wherein $R^3$ is a hydrogen atom, a vinyl group, an alkyl group, a phenyl group, a (meth)acryloyl group, an ally group, or an oxirane ring-containing group; the substituents selected for $R^3$ may be identical with or different from one another; X is a hydroxyl group, a hydrogen atom, a chlorine atom, or an alkoxyl group and the substituents selected for X may be identical with or different from one another; further, p denotes a number of 0-30) to yield a curable cage-type silicone copolymer characterized by having a constituent unit represented by the following general formula (1-1):

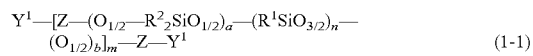

$$Y^1 - [Z - (O_{1/2} - R^2_2SiO_{1/2})_a - (R^1SiO_{3/2})_n - (O_{1/2})_b]_m - Z - Y^1 \quad (1-1)$$

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$, n denotes a number of 8-14, and m denotes a number of 1-2,000; Z is a divalent group represented by the following general formula (2)

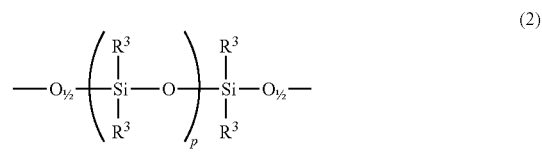

$$(2)$$

wherein $R^3$ is a hydrogen atom, a vinyl group, an alkyl group, a phenyl group, a (meth)acryloyl group, an allyl group, or an oxirane ring-containing group, the substituents selected for $R^3$ may be identical with or different from one another, and p denotes a number of 0-30; and $Y^1$ is a monovalent group represented by the following general formula (3), (4), or (5)

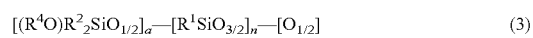

$$[(R^4O)R^2_2SiO_{1/2}]_a - [R^1SiO_{3/2}]_n - [O_{1/2}] \quad (3)$$

$$[R^4O_{1/2}]_b - [R^1SiO_{3/2}]_n - [O_{1/2}] - \quad (4)$$

$$(R^4O_{1/2}) - \quad (5)$$

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from each other; $R^4$ is selected from a hydrogen atom, a methyl group, and an ethyl group; a and b each is a number of 0-3 and n denotes a number of 8-14.

The process for producing a curable cage-type silicone copolymer represented by general formula (1-1) by the condensation reaction of a cage-type siloxane compound containing an alkoxyl group or silanol group represented by general formula (7) with a compound represented by general formula (8) varies depending on whether a cage-type siloxane compound containing an alkoxyl group represented by general formula (7-1) or a cage-type siloxane compound containing a silanol group represented by general formula (7-2) is used. Furthermore, in the case where a cage-type siloxane compound containing a silanol group represented by general formula (7-2) is used, the process also varies with the kind of substituent X in a compound represented by general formula (8).

When a siloxane compound containing an alkoxyl group represented by general formula (7-1) is subjected to condensation reaction with a compound represented by general formula (8) wherein X is a hydroxyl group, that is, when a siloxane compound containing an alkoxyl group represented by general formula (7-1) is allowed to react with a compound represented by the following general formula (8-1)

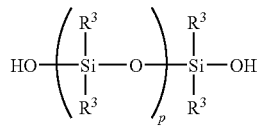

(8-1)

(wherein $R^3$ is a hydrogen atom, a vinyl group, an alkyl group, a phenyl group, a (meth)acryloyl group, an allyl group, or an oxirane ring-containing group, the substituents selected for $R^3$ may be identical with or different from one another, and p denotes a number of 0-30), the following procedure is preferably followed. A mixture of 1 mole of a cage-type siloxane compound containing an alkoxyl group represented by general formula (7-1) and 0.5-10 moles, preferably 0.5-3.0 moles, of a silanediol represented by the aforementioned general formula (8-1) or α,ω-disilanolsiloxane is subjected to dealcoholization condensation reaction in a solvent consisting of one or both of a non-polar solvent and an ether-based solvent in the presence of a catalyst to yield a curable cage-type silicone copolymer with a constituent unit represented by general formula (1-1).

Concretely, the dealcoholization condensation reaction between a cage-type siloxane compound containing an alkoxyl group represented by general formula (7-1) and a silanediol represented by the aforementioned general formula (8) or am-disilanolsiloxane is effected, for example, under the following conditions. When a cage-type siloxane compound containing an alkoxyl group represented by general formula (7), a compound represented by general formula (8-1), and a catalyst are dissolved in a solvent consisting of one or both of a non-polar solvent and an ether-based solvent, the concentration of a cage-type siloxane compound containing an alkoxyl group is preferably set at 0.1-2.0M (mol/l). The reaction temperature is set preferably at 0-130° C., more preferably at 50-110° C. When the reaction temperature is below 0° C., the reaction rate drops and the reaction consumes a longer time. On the other hand, when the reaction temperature is above 130° C., cleavage of the cage structure occurs and a gel-like solid forms as a result of a complicated condensation reaction. The reaction time is preferably 2 hours or more. The reaction may not proceed to completion when the reaction time is short.

Upon completion of the reaction, the reaction solution is made neutral or slightly acidic and water or the reaction solution containing water is separated. This separation is effected by a procedure which consists, for example, of washing the solution with an aqueous sodium chloride solution or the like to remove water and other impurities sufficiently and then drying the solution with a drying agent such as anhydrous magnesium sulfate. When an ether-based solvent is used, the solvent is removed by a means such as evaporation under reduced pressure; thereafter, a non-polar solvent is added to the residue to dissolve the polycondensation product and the resulting solution is washed and dried as described above.

Examples of the silanediols represented by general formula (8-1) wherein p is 0 include dimethylsilanediol, ethylmethylsilanediol, phenylmethylsilanediol, diethylsilanediol, ethylallylsilanediol, styrylmethylsilanediol, divinylsilanediol, vinylmethylsilanediol, 3-glycidoxypropylmethylsilanediol, 3-acryloxypropylmethylsilanediol, 3-methacryloxypropylmethylsilanediol, and diphenylsilanediol.

Examples of α,ω-disilanolsiloxane represented by general formula (8-1) wherein p is 1-30 include silanol-terminated polydimethylsiloxane, silanol-terminated polydiphenylsiloxane, and silanol-terminated diphenylsiloxane-methylsiloxane copolymers.

The organic solvents to be used in the dealcoholization condensation reaction between a cage-type siloxane compound containing an alkoxyl group represented by general formula (7-1) and a silanediol represented by general formula (8) or α,ω-disilanolsiloxane may be selected freely from organic solvents that are inert to these reactants. Of such organic solvents, examples of non-polar solvents include hydrocarbons such as hexane, toluene, xylene, and benzene. Examples of ether-based solvents include diethyl ether and tetrahydrofuran. Of these examples, toluene is preferred as a solvent. A mixture of an ether-based solvent and a non-polar solvent works as well. The organic solvent is used in the range of 0.01-10M (mol/l), preferably in the range of 0.1-1M (mol/l), per 1 mole of a structural unit represented by general formula (2).

The catalysts to be used in the dealcoholization condensation reaction of a cage-type siloxane compound containing an alkoxyl group represented by general formula (7-1) and a silanediol represented by general formula (8-1) or α,ω-disilanolsiloxane include alkali metal hydroxides such as potassium hydroxide, sodium hydroxide, and cesium hydroxide, quaternary ammonium hydroxides such as tetramethylammonium hydroxide, tetraethylammonium hydroxide, tetrabutylammonium hydroxide, benzyltrimethylammonium hydroxide, and benzyltriethylammonium hydroxide, catalysts based on metal-containing organic compounds such as tetraethoxytitanium, tetrabutoxytitanium, tin oxide, dibutyltin oxide, zinc acetate dihydrate, lead acetate trihydrate, lead oxide, aluminum acetate, manganese acetate tetrahydrate, cobalt acetate tetrahydrate, cadmium acetate, dibutyltin laurate, dibutyltin maleate, dioctyltin mercaptide, stannous octoate, and lead octenoate, triethylenediamine, tetramethylguanidine, 2-(dimethylaminomethyl)phenol, N,N,N',N'-tetramethylhexane-1,6-diamine, 1,8-diazabicyclo[5.4.0]undecene-7, p-toluenesulfonic acid, and trifluoroacetic acid. Of these, tetramethylammonium is preferred for its high catalytic activity.

The condensation reaction of a siloxane compound containing a silanol group represented by general formula (7-2) with a compound represented by general formula (8) wherein X is an alkoxyl group, that is, the reaction of a siloxane compound containing a silanol group represented by general formula (7-2) with a compound represented by the following general formula (8-2)

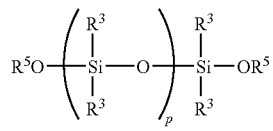

(8-2)

(wherein $R^3$ is a hydrogen atom, a vinyl group, an alkyl group, a phenyl group, a (meth)acryloyl group, an allyl group, or an oxirane ring-containing group; the substituents selected for $R^3$ may be identical with or different from one another; $R^5$ is a methyl group, an ethyl group, or a propyl group and the substituents selected for $R^5$ may be identical with or different from one another; p denotes a number of 0-30) is carried out preferably as follows. A cage-type siloxane compound containing a silanol group represented by general formula (7-2)

and a dialkoxysilane represented by the aforementioned general formula (8-2) or α,ω-dialkoxysiloxane are subjected to dealcoholization condensation at a ratio of 1 mole of the former to 0.5-10 moles, preferably 0.5-3.0 moles, of the latter in the presence of a catalyst in a solvent consisting of one or both of a non-polar solvent and an ether-based solvent to yield a curable cage-type silicone copolymer with a constituent unit represented by general formula (1-1).

Concretely, the dealcoholization condensation of a cage-type siloxane compound containing a silanol group represented by general formula (7-2) and a dialkoxysilane represented by the aforementioned general formula (8-2) or α,ω-dialkoxysiloxane can be carried out, for example, under the following conditions. When a cage-type siloxane compound containing a silanol group represented by general formula (7-2), a dialkoxysilane represented by the aforementioned general formula (8-2) or α,ω-dialkoxysiloxane, and a catalyst are dissolved in a solvent consisting of one or both of a non-polar solvent and an ether-based solvent, it is preferable to control the amount of the solvent so that the concentration of the cage-type siloxane compound containing a silanol group becomes 0.1-2.0M (mol/l). The reaction temperature is preferably 0-130° C., more preferably 50-110° C. When the reaction temperature is below 0° C., the reaction rate drops and the reaction consumes a longer time. On the other hand, when the reaction temperature is above 130° C., cleavage of the cage structure occurs and a gel-like solid forms as a result of a complicated condensation reaction. The reaction time is preferably 2 hours or more. The reaction may not proceed to completion when the reaction time is short.

Upon completion of the reaction, the reaction solution is made neutral or slightly acidic and water or the reaction solvent containing water is separated. This separation is effected by a procedure which consists, for example, of washing the solution with an aqueous sodium chloride solution or the like to remove water and other impurities sufficiently and then drying with a drying agent such as anhydrous magnesium sulfate. In the case where an ether-based solvent is used, a means of evaporation under reduced pressure can be adopted; after removal of the ether-based solvent, a non-polar solvent is added to the residue to dissolve the polycondensation product and the resulting solution is washed and dried as described above.

Examples of the dialkoxysilanes represented by general formula (8-2) wherein p is 0 include dimethyldimethoxysilane, diethyldimethoxysilane, phenylmethyldimethoxysilane, vinylmethyldimethoxysilane, ethylallyldimethoxysilane, styrylmethyldimethoxysilane, divinyldimethoxysilane, 3-glycidoxypropylmethyldimethoxysilane, 3-methacryloxypropyldimethoxysilane, 3-acryloxypropyldimethoxysilane, dimethyldiethoxysilane, diethyldiethoxysilane, phenylmethyldiethoxysilane, vinylmethyldiethoxysilane, ethylallyldiethoxysilane, styrylmethyldiethoxysilane, divinyldiethoxysilane, 3-glycidoxypropylmethyldiethoxysilane, 3-methacryloxypropyldiethoxysilane, and 3-acryloxypropyldiethoxysilane.

Examples of the α,ω-dialkoxysiloxanes represented by general formula (8-2) wherein p is 1-30 include 1,3-dimethoxytetramethyldisiloxane, 1,3-diethoxytetramethyldisiloxane, 1,5-dimethoxyhexamethyltrisiloxane, 1,7-dimethoxyoctamethyltetrasiloxane, 1,5-diethoxyhexamethyltrisiloxane, and 1,7-diethoxyoctamethyltetrasiloxane.

The solvents and the catalysts to be used in the dealcoholization condensation of a cage-type siloxane compound containing a silanol group represented by general formula (7-2) and a dialkoxysilane represented by the aforementioned general formula (8-2) or α,ω-dialkoxysiloxane may be the same as those used in the dealcoholization condensation of a cage-type siloxane compound containing an alkoxyl group represented by general formula (7-1) and a silanediol represented by general formula (8-1) or α,ω-disilanolsiloxane described earlier.

The condensation reaction of a siloxane compound containing a silanol group represented by general formula (7-2) and a compound represented by general formula (8) wherein X is a hydrogen atom, that is, the reaction of a siloxane compound containing a silanol group represented by general formula (7-2) with a compound represented by the following general formula (8-3)

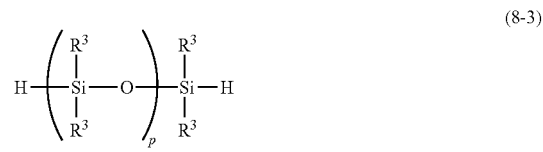

(8-3)

(wherein $R^3$ is a hydrogen atom, a vinyl group, an alkyl group, a phenyl group, a (meth)acryloyl group, an allyl group, or an oxirane ring-containing group, the substituents selected for $R^3$ may be identical with or different from one another, and p denotes a number of 0-30) is preferably carried out as follows. A cage-type siloxane compound containing a silanol group represented by general formula (7-2) and a dihydrogensilane represented by the aforementioned general formula (8-3) or α,ω-dihydrogensiloxane are subjected to dehydrogenation condensation at a ratio of 1 mole of the former to 0.5-10 moles, preferably 0.5-3.0 moles, of the latter in the presence of a catalyst in a solvent consisting of one of both of a non-polar solvent and an ether-based solvent to yield a curable cage-type silicone copolymer with a constituent unit represented by general formula (1-1).

Concretely, the reaction of a cage-type siloxane compound containing a silanol group represented by general formula (7-2) with a dihydrogensilane represented by general formula (8-2) or α,ω-dihydrogensiloxane can be carried out, for example, under the following conditions. When a cage-type siloxane compound containing a silanol group represented by general formula (7-2), a dihydrogensilane or α,ω-dihydrogensiloxane, and a catalyst are dissolved in a solvent consisting of one or both of a non-polar solvent and an ether-based solvent, it is preferable to control the amount of the solvent so that the concentration of the cage-type siloxane compound containing a silanol group becomes 0.1-2.0M (mol/l). The reaction temperature is preferably 0-100° C., more preferably 20-80° C. When the reaction temperature is below 0° C., the reaction rate drops and the reaction consumes a longer time. On the other hand, when the reaction temperature is above 100° C., a complicated condensation reaction proceeds and a gel-like solid forms. The reaction time is preferably 2 hours or more. The reaction may not proceed to completion when the reaction time is short.

Upon completion of the reaction, the reaction solution is made neutral or slightly acidic and water or the reaction solvent containing water is separated. During this time, the hydrolysis converts non-silanol terminal groups to silanol groups. The separation of water or the solvent containing water is effected by a procedure which consists, for example, of washing the solution with an aqueous sodium chloride solution or the like to remove water and other impurities sufficiently and then drying with a drying agent such as anhydrous magnesium sulfate. In the case where an ether-based solvent is used, a means of evaporation under reduced pressure can be adopted; after removal of the ether-based solvent, a non-polar solvent is added to the residue to dissolve the polycondensation product and the resulting solution is washed and dried as described above.

Examples of the dihydrogensilanes represented by general formula (8-3) wherein p is 0 include diethylsilane and diphenylsilane.

Examples of α,ω-dihydrogensiloxanes represented by general formula (8-3) wherein p is 1-30 include 1,1,3,3-tetramethyldisiloxane, 1,1,3,3-tetracyclopentyldisiloxane, 1,1,3,3-tetraisopropyldisiloxane, 1,1,3,3,5,5-hexamethyltrisiloxane, 1,1,3,3,5,5,7,7-octamethyltetrasiloxane, hydrogen-terminated polydimethylsiloxane, hydrogen-terminated polymethylphenylsiloxane, hydrogen-terminated methylsiloxane-dimethylsiloxane copolymer, hydrogen-terminated methylsiloxane-methylphenylsiloxane copolymer, and hydrogen-terminated phenyl(dimethylhydrosiloxy)siloxane.

The organic solvents to be used for a compound represented by general formula (8) wherein X is a hydrogen atom may be selected freely from organic solvents that are inert to dihydrogensilanes or α,ω-dihydrogensiloxanes. Examples of the non-polar solvents useful for this purpose include hydrocarbons such as hexane, toluene, xylene, and benzene. Examples of the ether-based solvents include diethyl ether and tetrahydrofuran. Of these, toluene is used preferably. A mixture of a polar solvent and an ether-based solvent works as well. The organic solvent is preferably used at a rate of 0.01-10 (mol/l), preferably 0.1-1M (mol/l), per 1 mole of a structural unit represented by general formula (2).

The catalysts to be used for a compound represented by general formula (8) wherein X is a hydrogen atom include tetraethoxytitanium, tetrabutoxytitanium, and hydroxylamine compounds such as hydroxylamine, N-methylhydroxylamine, N,N-dimethylhydroxylamine, N-ethylhydroxylamine, and N,N-diethylhydroxylamine. Of these, N,N-diethylhydroxylamine is preferred.

The condensation reaction of a siloxane compound containing a silanol group represented by general formula (7-2) and a compound represented by general formula (8) wherein X is a chlorine atom, that is, the reaction of a siloxane compound containing a silanol group represented by general formula (7-2) with a compound represented by the following general formula (8-4)

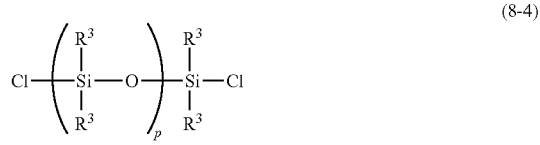

(8-4)

(wherein $R^3$ is a hydrogen atom, a vinyl group, an alkyl group, a phenyl group, a (meth)acryloyl group, an allyl group, or an oxirane ring-containing group, the substituents selected for $R^3$ may be identical with or different from one another, and p denotes a number of 0-30) is preferably carried out as follows. A cage-type siloxane compound containing a silanol group represented by general formula (7-2) and a dichlorosilane represented by the aforementioned general formula (8-4) or α,ω-dichlorosiloxane are subjected to dehydrochlorination condensation at a ratio of 1 mole of the former to 0.5-10 moles, preferably 0.5-3.0 moles, of the latter in the presence of a catalyst in a solvent consisting of one or both of a non-polar solvent and an ether-based solvent to yield a curable cage-type silicone copolymer with a constituent unit represented by general formula (1-1).

Concretely, the dehydrochlorination condensation of a cage-type siloxane compound containing a silanol group represented by general formula (7-2) and a dichlorosilane represented by general formula (8-4) or α,ω-dichlorosiloxane can be carried out, for example, under the following conditions. A dichlorosilane or α,ω-dichlorosiloxane is dissolved in a solvent consisting of one or both of a non-polar solvent and an ether-based solvent and triethylamine is added to this solution at a rate of 2 equivalents or more per 1 equivalent of the dichlorosilane or α,ω-dichlorosiloxane; alternatively, dichlorosilane or α,ω-dichlorosiloxane is dissolved in an amine-based solvent which functions dually as a solvent and a catalyst. To either of these solutions is added dropwise a solution of the cage-type siloxane compound containing a silanol group in a solvent consisting of one or both of a non-polar solvent and an ether-based solvent in an atmosphere of inert gas such as nitrogen at room temperature. Thereafter, the reaction solution is preferably stirred at room temperature for 2 hours or more. The reaction may not proceed to completion when the reaction time is short. Upon completion of the reaction, toluene and water are added to the reaction solution thereby dissolving a curable cage-type silicone copolymer with a constituent unit represented by general formula (1-1) in the toluene and dissolving the excess chlorosilane and the by-products hydrochloric acid and salts thereof in the aqueous layer for removal. The organic layer is dried over a drying agent such as magnesium sulfate and the base and the solvent used are concentrated under reduced pressure and removed.

Examples of the dichlorosilanes represented by general formula (8-4) wherein p is 0 include allyldichlorosilane, allylhexyldichlorosilane, allylmethyldichlorosilane, allylphenyldichlorosilane, methyldichlorosilane, dimethyldichlorosilane, ethyldichlorosilane, methylvinyldichlorosilane, ethylmethyldichlorosilane, ethoxymethyldichlorosilane, divinyldichlorosilane, diethyldichlorosilane, methylpropyldichlorosilane, diethoxydichlorosilane, butylmethyldichlorosilane, phenyldichlorosilane, diallyldichlorosilane, methylpentyldichlorosilane, methylphenyldichlorosilane, cyclohexylmethyldichlorosilane, hexylmethyldichlorosilane, phenylvinyldichlorosilane, 6-methyldichlorosilyl-2-norbornane, 2-methyldichlorosilylnorbornane, 3-methacryloxypropyldichloromethylsilane, heptylmethyldichlorosilane, dibutyldichlorasilane, methylphenetyldichlorosilane, methyloctyldichlorosilane, t-butylphenyldichlorosilane, decylmethyldichlorosilane, diphenyldichlorosilane, dihexyldichlorosilane, dodecylmethyldichlorosilane, and methyloctadecyldichlorosilane.

Examples of α,ω-dichlorosiloxanes represented by general formula (8-4) wherein p is 1-30 include 1,1,3,3-tetramethyl-1,3-dichlorosiloxane, 1,1,3,3-tetracyclopentyl-1,3-dichlorosiloxane, 1,1,3,3-tetraisopropyl-1,3-dichlorosiloxane, 1,1,3,3,5,5-hexamethyl-1,5-dichlorotrisiloxane, and 1,1,3,3,5,5,7,7-octamethyl-1,7-dichlorotetrasiloxane.

The organic solvents to be used for a compound represented by general formula (8) wherein X is a chlorine atom may be selected freely from organic solvents that are inert to dichlorosilanes or α,ω-disilanolsiloxanes. Of such solvents, examples of non-polar solvents include hydrocarbons such as hexane, toluene, xylene, and benzene. Examples of ether-based solvents include diethyl ether and tetrahydrofuran. Of these examples, the ether-based solvents are preferable from the viewpoint of contribution to the structural control by the solvating effect and tetrahydrofuran is particularly preferable. Moreover, it is possible to use an amine-based solvent, either singly or mixed, dually as a solvent and a base. Examples of such amine-based solvents include pyridine, triethylamine, aniline, and N,N-diisopropylamine. In the case where an amine-based solvent is not used, a base such as triethylamine is added. The solvent is used in the range of 0.01-10M (mol/l), preferably in the range of 0.1-1M, per 1 mole of a cage-type siloxane compound containing a silanol group represented by general formula (7-2).

The curable cage-type silicone copolymer obtained as described above is characterized by having a constituent unit represented by the following general formula (1-1):

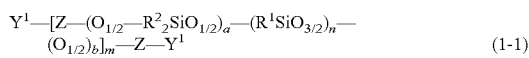
$$Y^1—[Z—(O_{1/2}—R^2{}_2SiO_{1/2})_a—(R^1SiO_{3/2})_n—(O_{1/2})_b]_m—Z—Y^1 \qquad (1\text{-}1)$$

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$, n denotes a number of 8-14, and m denotes a number of 1-2,000; Z is a divalent group represented by the following general formula (2)

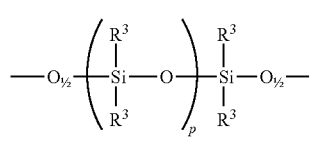

(2)

wherein $R^3$ is a hydrogen atom, a vinyl group, an alkyl group, a phenyl group, a (meth)acryloyl group, an allyl group, or an oxirane ring-containing group, the substituents selected for $R^3$ may be identical with or different from one another, and p denotes a number of 0-30; and $Y^1$ is a monovalent group selected from the following general formulas (3), (4), and (5)

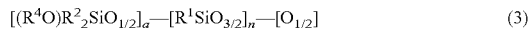
$$[(R^4O)R^2{}_2SiO_{1/2}]_a—[R^1SiO_{3/2}]_n—[O_{1/2}] \qquad (3)$$

$$[R^4O_{1/2}]_b—[R^1SiO_{3/2}]_n—[O_{1/2}]— \qquad (4)$$

$$(R^4O_{1/2})— \qquad (5)$$

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from each other; $R^4$ is selected from a hydrogen atom, a methyl group, and an ethyl group; a and b each is a number of 0-3 and n denotes a number of 8-14.

Furthermore, the condensation of a curable cage-type silicone copolymer represented by general formula (1-1) wherein $R^4$ in the terminal $Y^1$ is a hydrogen atom, that is, a silanol-terminated curable cage-type silicone copolymer, and a compound represented by the following general formula (9)

$$R^2{}_3Si—X \qquad (9)$$

(wherein $R^2$ is a hydrogen atom, a vinyl group, an alkyl group, a phenyl group, a (meth)acryloyl group, an allyl group, or an oxirane ring-containing group, the substituents selected for $R^2$ may be identical with or different from one another, and X is a hydrogen atom, a chlorine atom, or an alkoxyl group) yields a curable cage-type silicone copolymer with a constituent unit represented by general formula (1-2):

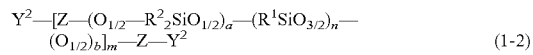
$$Y^2—[Z—(O_{1/2}—R^2{}_2SiO_{1/2})_a—(R^1SiO_{3/2})_n—(O_{1/2})_b]_m—Z—Y^2 \qquad (1\text{-}2)$$

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$, n denotes a number of 8-14, and m denotes a number of 1-2,000; Z is a divalent group represented by the following general formula (2)

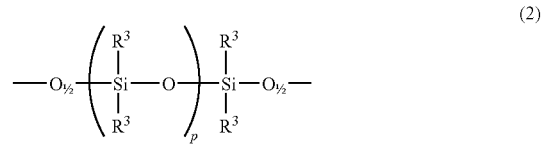

(2)

wherein $R^3$ is a hydrogen atom, a vinyl group, an alkyl group, a phenyl group, a (meth)acryloyl group, an allyl group, or an oxirane ring-containing group, the substituents selected for $R^3$ may be identical with or different from one another, and p denotes a number of 0-30; and $Y^2$ is a monovalent group represented by the following general formula (6)

$$(R^2{}_3SiO_{1/2})— \qquad (6)$$

wherein $R^2$ is a vinyl group, an alkyl group, a phenyl group, a (meth)acryloyl group, an allyl group, or an oxirane ring-containing group and the substituents selected for $R^2$ may be identical with or different from one another.

Now, it is possible to convert a curable cage-type silicone copolymer represented by general formula (1-1) wherein $R^4$ in the terminal $Y^1$ is a methyl group or an ethyl group, that is, an alkoxyl-terminated curable cage-type silicone copolymer, to a silanol-terminated curable cage-type silicone copolymer by converting the terminal alkoxyl group to the silanol group by hydrolysis in the presence of an acid catalyst or a basic catalyst. The procedure for the hydrolysis here may be the same as the one cited earlier as an example in the process for producing a cage-type siloxane compound containing a silanol group.

In the process for producing a curable cage-type silicone copolymer by the condensation of a curable cage-type silicone copolymer represented by general formula (1-1) wherein $R^4$ in the terminal $Y^1$ is a hydrogen atom, that is, a silanol-terminated curable cage-type silicone copolymer, and a compound represented by the aforementioned general formula (9), the process varies with the kind of X in general formula (9) as will be explained below.

First, in the case where X in general formula (9) is an alkoxyl group, that is, the compound is represented by the following general formula (9-1)

$$R^2{}_3Si—OR^5 \qquad (9\text{-}1)$$

(wherein $R^2$ is a hydrogen atom, a vinyl group, an alkyl group, a phenyl group, a (meth)acryloyl group, an allyl group, or an oxirane ring-containing group and the substituents selected for $R^2$ may be identical with or different from one another, $R^5$ is a methyl group, an ethyl group, or a propyl group, and the substituents selected for $R^5$ may be identical with or different from one another), it is preferable to proceed as follows. A curable cage-type silicone copolymer represented by general formula (1-1) wherein $R^4$ in the terminal $Y^1$ is a hydrogen atom, that is, a silanol-terminated curable cage-type silicone copolymer, and an alkoxysilane represented by the aforementioned general formula (9-1) are subjected to dealcoholization condensation at a ratio of 1 mole of the former to 2-100 moles of the latter in the presence of a catalyst in a solvent consisting of one or both of a non-polar solvent and an ether-based solvent to yield a curable cage-type silicone copolymer with a constituent unit represented by general formula (1-2). Here, an alkoxysilane is used preferably in an amount of 2-30 moles per 1 mole of a curable cage-type silicone copolymer with a constituent unit represented by general formula (1-1). The dealcoholization condensation reaction may be carried out by the procedure earlier cited as an example in the dealcoholization condensation of a siloxane compound containing a silanol group represented by general formula (7-2) and a dialkoxysilane represented by general formula (8-2) or α,ω-dichlorosiloxane for the production of a curable cage-type silicone copolymer with a constituent unit represented by general formula (1-1).

Only in the case where a curable cage-type silicone copolymer with a constituent unit represented by general formula (1-1) is produced by the dealcoholization condensation of a cage-type siloxane compound containing an alkoxyl group represented by general formula (7-1) and a silanediol represented by general formula (8-1) or α,ω-disilanolsiloxane or by the dealcoholization condensation of a cage-type siloxane compound containing a silanol group represented by general formula (7-2) and a dialkoxysilane represented by general formula (8-2) or α,ω-dialkoxysiloxane, an alkoxysilane represented by general formula (9-1) is added to the reaction system without taking out a curable cage-type silicone copolymer with a constituent unit represented by general formula (1-1) and the reaction is allowed to proceed to yield a curable cage-type silicone copolymer with a constituent unit represented by general formula (1-2).

Examples of the alkoxysilanes represented by general formula (9-1) include trimethylmethoxysilane, vinyldimethylmethoxysilane, dimethylmethoxysilane, phenyldimethylmethoxysilane, phenylmethoxysilane, triethylmethoxysilane, trivinylmethoxysilane, methyldivinylmethoxysilane, allyldimethylmethoxysilane, 3-methacryloxypropyldimethylmethoxysilane, 3-acryloxypropyldimethylmethoxysilane, styryldimethylmethoxysilane, trimethylethoxysilane, vinyldimethylethoxysilane, dimethylethoxysilane, phenyldimethylethoxysilane, phenylethoxysilane, triethylethoxysilane, trivinylethoxysilane, methyldivinylethoxysilane, allyldimethylethoxysilane, 3-methacryloxypropyldimethylethoxysilane, 3-acryloxypropyldimethylethoxysilane, styryldimethylethoxysilane, trimethylpropoxysilane, vinyldimethylpropoxysilane, dimethylpropoxysilane, phenyldimethylpropoxysilane, phenylpropoxysilane, triethylpropoxysilane, trivinylpropoxysilane, methyldivinylpropoxysilane, allyldimethylpropoxysilane, 3-methacryloxypropyldimethylpropoxysilane, 3-acryloxypropyldimethylpropoxysilane, styryldimethylpropoxysilane, trimethylisopropoxysilane, vinyldimethylisopropoxysilane, dimethylisopropoxysilane, phenyldimethylisopropoxysilane, phenylisopropoxysilane, triethylisopropoxysilane, trivinylisopropoxysilane, methyldivinylisopropoxysilane, allyldimethylisopropoxysilane, 3-methacryloxypropyldimethylisopropoxysilane, 3-acryloxypropyldimethylisopropoxysilane, and styryldimethylisopropoxysilane.

Second, in the case where X in general formula (9) is a hydrogen atom, that is, the compound is represented by the following general formula (9-2)

$$R^2_3Si-H \qquad (9-2)$$

(wherein $R^2$ is a hydrogen atom, a vinyl group, an alkyl group, a phenyl group, a (meth)acryloyl group, an allyl group, or an oxirane ring-containing group and the substituents selected for $R^2$ may be identical with or different from one another), it is preferable to proceed as follows. A curable cage-type silicone copolymer represented by general formula (1-1) wherein $R^4$ in the terminal $Y^1$ is a hydrogen atom, that is, a silanol-terminated curable cage-type silicone copolymer, and a hydrogensilane represented by the aforementioned general formula (9-2) are subjected to dehydrogenation condensation at a ratio of 1 mole of the former to 2-100 moles of the latter in the presence of a catalyst in a solvent consisting of one or both of a non-polar solvent and an ether-based solvent to yield a curable cage-type silicone copolymer with a constituent unit represented by general formula (1-2). Here, a hydrogensilane is used in an amount of 2-30 moles per 1 mole of a curable cage-type silicone copolymer with a constituent unit represented by general formula (1-1). The dehydrogenation condensation reaction may be carried out by the procedure earlier cited as an example in the dehydrogenation condensation of a siloxane compound containing a silanol group represented by general formula (7-2) and a dihydrogensilane represented by general formula (8-3) or am-dihydrogensiloxane for the production of a curable cage-type silicone copolymer with a constituent unit represented by general formula (1-1).

Only in the case where a curable cage-type silicone copolymer with a constituent unit represented by general formula (1-1) is produced by the dehydrogenation condensation of a cage-type siloxane compound containing a silanol group represented by general formula (7-2) and a dihydrogensilane represented by general formula (8-3) or α,ω-dihydrogensiloxane, an alkoxysilane represented by general formula (9-1) is added to the reaction system without taking out a curable cage-type silicone copolymer with a constituent unit represented by general formula (1-1) and the reaction is allowed to proceed to yield a curable cage-type silicone copolymer with a constituent unit represented by general formula (1-2).

Examples of the hydrogensilanes represented by general formula (9-2) include trimethylsilane, vinyldimethylsilane, phenyldimethylsilane, tirethylsilane, trivinylsilane, methyldivinylsilane, allyldimethylsilane, 3-methacryloxpropyldimethylsilane, 3-acryloxypropyldimethylsilane, styryldimethylsilane, dimethylpropylsilane, dimethylisopropylsilane, t-butyldimethylsilane, benzyldimethylsilane, tripropylsilane, tributylsilane, diphenylvinylsilane, and triphenylsilane.

Third, in the case where X in general formula (9) is a chlorine atom, that is, the compound is represented by the following general formula (9-3)

$$R^2_3Si-Cl \qquad (9-3)$$

(wherein $R^2$ is a hydrogen atom, a vinyl group, an alkyl group, a phenyl group, a (meth)acryloyl group, an allyl group, or an oxirane ring-containing group and the substituents selected for $R^2$ may be identical with or different from one another), it is preferable to proceed as follows. A cage-type curable silicone copolymer represented by general formula (1-1) wherein $R^4$ in the terminal $Y^1$ is a hydrogen atom, that is, a silanol-terminated curable cage-type silicone copolymer, and a chlorosilane represented by the aforementioned general formula (9-3) are subjected to dehydrochlorination condensation at a ratio of 1 mole of the former to 2-100 moles of the latter in the presence of a catalyst in a solvent consisting of one or both of a non-polar solvent and an ether-based solvent to yield a curable cage-type silicone copolymer with a constituent unit represented by general formula (1-2). Here, a chlorosilane is used in an amount of 2-30 moles per 1 mole of a curable cage-type silicone copolymer with a constituent unit represented by general formula (1-1). The dehydrochlorination condensation reaction may be carried out by the procedure earlier cited as an example in the dehydrochlorination condensation of a siloxane compound containing a silanol group represented by general formula (7-2) and a dichlorosilane represented by general formula (8-4) or α,ω-dichlorosiloxane for the production of a curable cage-type silicone copolymer with a constituent unit represented by general formula (1-1).

Only in the case where a curable cage-type silicone copolymer with a constituent unit represented by general formula (1-1) is produced by the dehydrochlorination condensation of a cage-type siloxane compound containing a silanol group represented by general formula (7-2) and a dichlorosilane represented by general formula (8-4) or α,ω-dihydrogensiloxane, an alkoxysilane represented by general formula (9-1) is added to the reaction system without taking out a curable cage-type silicone copolymer with a constituent unit represented by general formula (1-1) and the reaction is allowed to proceed to yield a curable cage-type silicone copolymer with a constituent unit represented by general formula (1-2).

Examples of the chlorosilanes represented by general formula (9-3) include trimethylchlorosilane, vinyldimethylchlorosilane, dimethylchlorosilane, phenyldimethylchlorosilane, phenylchlorosilane, triethylchlorosilane, trivinylchlorosilane, methyldivinylchlorosilane, allyldimethylchlorosilane, 3-methacryloxypropyldimethylchlorosilane, 3-acryloxypropyldimethylchlorosilane, styryldimethylchlorosilane, dimethylpropylchlorosilane, dimethylisopropylchlorosilane, t-butyldimethylchlorosilane, benzyldimethylchlorosilane, tripropylchlorosilane, tributylchlorosilane, diphenylvinylchlorosilane, and triphenylchlorosilane.

According to this invention, a curable resin composition may be obtained by incorporating a hydrosilylation catalyst or a radical initiator or both in a curable cage-type silicone copolymer represented by general formula (1). This curable resin composition is cured by heat or light to effect hydrosilylation or radical polymerization to yield a cured product (molded article). Alternatively, a curable resin composition may be obtained by incorporating a compound having a hydrogen atom on a silicon atom or a compound having an unsaturated group in the molecule in addition to a hydrosilylation catalyst and a radical initiator. That is, for the purpose of curing a curable resin to yield a molded article or improving the properties of a molded article, it is allowable to incorporate additives such as hydrosilylation catalysts, thermal polymerization initiators, thermal polymerization accelerators, photopolymerization initiators, auxiliary agents for photopolymerization initiation, sensitizers, and the like in a curable resin composition to accelerate the reaction.

The compound having a hydrogen atom on a silicon atom to be used together with a curable cage-type silicone copolymer represented by general formula (1) in formulating a curable resin composition is an oligomer or a monomer having at least one hydrosilylatable hydrogen atom on a silicon atom. The oligomers having a hydrogen atom on a silicon atom include polyhydrogensiloxanes, polydimethylhydrosiloxysiloxanes and copolymers thereof, and dimethylhydrosiloxy-terminated siloxanes. The monomers having a hydrogen atom on a silicon atom include cyclic siloxanes such as tetra methylcyclotetrasiloxane and pentamethylcyclopentasiloxane, dihydrodisiloxanes, trihydromonosilanes, dihydromonosilanes, monohydromonosilanes, and dimethylsiloxysiloxanes. Two kinds of more of these compounds may be mixed in use.

The unsaturated group-containing compounds to be used together with a curable cage-type silicone copolymer represented by general formula (1) in formulating a curable resin composition are divided roughly into reactive oligomers with 2-20 repeating structural units and reactive monomers of low molecular weight and low viscosity. The unsaturated group-containing compounds are also divided roughly into monofunctional unsaturated compounds containing a single unsaturated group and polyfunctional unsaturated compounds containing 2 or more unsaturated groups.

The reactive oligomers include polyvinyl siloxanes, polydimethylvinylsiloxysiloxanes and copolymers thereof, dimethylvinylsiloxy-terminated siloxanes, epoxy acrylates, epoxidized acrylates, urethane acrylates, unsaturated polyesters, polyester acrylates, polyether acrylates, vinyl acrylate, polyene/thiol compositions, silicone acrylates, polybutadiene, and poly(styrylethyl methacrylate). There are monofunctional unsaturated compounds and polyfunctional unsaturated compounds.

The reactive monofunctional monomers include vinyl-substituted silicon compounds such as triethylvinylsilane and triphenylvinylsilane, cyclic olefins such as cyclohexene, styrene, vinyl acetate, N-vinylpyrrolidone, butyl acrylate, 2-ethylhexyl acrylate, n-hexyl acrylate, cyclohexyl acrylate, n-decyl acrylate, isobornyl acrylate, dicyclopentenyloxyethyl acrylate, phenoxyethyl acrylate, and trifluoroethyl methacrylate.

The reactive polyfunctional monomers include vinyl-substituted silicon compounds such as tetravinylsilane and divinyltetramethyldisiloxane, vinyl-substituted cyclic silicon compounds such as tetramethyltetravinylcyclotetrasiloxane and pentamethylpentavinylcyclopentasiloxane, acetylene derivatives such as bis(trimethylsilyl)acetylene and diphenylacetylene, cyclic polyenes such as norbornadiene, dicyclopentadiene, and cyclooctadiene, vinyl-substituted cyclic olefins such as vinylcyclohexene, divinylbenzenes, diethynylbenzenes, trimethylolpropane diallyl ether, pentaerythritol triallyl ether, and acrylates such as tripropylene glycol diacrylate, 1,6-hexanediol diacrylate, bisphenol A diglycidyl ether diacrylate, tetraethylene glycol diacrylate, neopentylglycol hydroxypivalate diacrylate, trimethylolpropane triacrylate, pentaerythritol triacrylate, pentaerythritol tetraacrylate, dipentaerythritol hexaacrylate, dimethylol-tricyclodecane diacrylate, 1,3-bis(methacryloxymethyl)-1,1,3,3-tetramethyldisiloxane, 1,3-bis(3-methacryloxypropyl)-1,1,3,3-tetramethyldisiloxane, 1,3-bis(acryloxymethyl)-1,1,3,3-tetramethyldisiloxane, and 1,3-bis(3-acryloxypropyl)-1,1,3,3-tetramethyldisiloxane.

A variety of reactive oligomers and monomers other than those cited above may be used as compounds having an unsaturated group in the molecule. They may be used singly or as a mixture of two kinds or more.

The compounds having a hydrogen atom on a silicon atom and the compounds having an unsaturated group in the molecule may respectively be used singly or as a mixture of two kinds or more in this invention.

According to this invention, a curable resin composition is obtained by incorporating a hydrosilylation catalyst and a radical initiator and, if necessary, a compound having a hydrogen atom on a silicon atom or a compound having an unsaturated group in a curable cage-type silicone copolymer represented by general formula (1) as described above. This curable resin composition is molded and cured to yield a molded article of this invention. That is, it is possible to obtain a cured product by hydrosilylation curing and radical polymerization of a curable resin composition.

The hydrosilylation catalyst is incorporated in the curable resin at a rate of 1-1000 ppm, preferably 20-500 ppm, as metal atom on a weight basis. The radical initiator, which is a photopolymerization initiator or a thermal polymerization initiator, is incorporated preferably at a rate of 0.1-10 parts by weight, more preferably 0.1-5 parts by weight, per 100 parts by weight of the curable resin. When the radical initiator is added in an amount of less than 0.1 part by weight, curing proceeds insufficiently to yield a molded article of lower strength and rigidity. On the other hand, when the amount added exceeds 10 parts by weight, there may arise such problems as discoloration of molded articles. The hydrosilylation catalysts or the radical initiators may be used singly or as a mixture of two kinds or more.

The hydrosilylation catalysts include catalysts based on platinum group metals such as platinum(IV) chloride, chloroplatinic acid, complexes of chloroplatinic acid with alcohols, aldehydes, or ketones, complexes of chloroplatinic acid with olefins, complexes of platinum with vinylsiloxanes, dicarbonyldicloroplatinum, palladium-based catalysts, and rhodium-based catalysts. Of these catalysts, chloroplatinic acid, complexes of chloroplatinic acid with olefins, and complexes of platinum with vinylsiloxanes are preferable from the viewpoint of catalytic activity. They may be used singly or as a mixture of two kinds or more.

The photopolymerization initiators useful for converting a curable resin composition to a photocurable resin composition include compounds derived from acetophenone, benzoin, benzophenone, thioxanthone, and acylphosphine oxides. Examples include trichloroacetophenone, diethoxyacetophenone, 1-phenyl-2-hydroxy-2-methylpropan-1-one, 1-hydroxycyclohexyl phenyl ketone, 2-methyl-1-(4-methylthiophenyl)-2-morpholinopropan-1-one, benzoin methyl ether, benzyl dimethyl ketal, benzophenone, thioxanthone, 2,4,6-trimethylbenzoyldiphenylphosphine oxide, methylphenyl glyoxylate, camphorquinone, benzil, anthraquinone, and Michler's ketone. The photopolymerization initiators may be used together with auxiliary agents for photopolymerization initiation and sensitizers that are known to display their effects when used in combination with photopolymerization initiators.

A variety of organic peroxides such as ketone peroxides, peroxyketals, hydroperoxides, dialkyl peroxides, diacyl peroxides, peroxydicarbonates, and peroxy esters are suitable for use as the aforementioned thermal polymerization initiators. Examples include cyclohexanone peroxide, 1,1-bis(t-hexaperoxy)cyclohexanone, cumene hydroperoxide, dicumyl peroxide, benzoyl peroxide, diisopropyl peroxide, and t-butyl peroxy-2-ethylhexanoate. However, the useful thermal polymerization initiators are not limited to these examples. Furthermore, they may be used singly or as a mixture of two kinds or more.

It is allowable to incorporate a variety of additives in a curable resin composition to the extent that such incorporation does not deviate from the object of this invention. Examples of such additives include organic/inorganic fillers, plasticizers, fire retardants, heat stabilizers, antioxidants, light stabilizers, ultraviolet absorbers, lubricants, antistatic agents, mold release agents, foaming agents, nucleating agents, colorants, crosslinking agents, dispersing agents, and resin components.

According to this invention, a curable cage-type silicone copolymer represented by general formula (1) is formed into a molded article by heating or photoirradiating a curable resin composition comprising the said curable silicone copolymer and a hydrosylilation catalyst or a radical polymerization initiator or both. When a cured product (molded article) is produced by heating, the molding temperature can be set at any point in a wide range from room temperature to around 200° C. by properly selecting a thermal polymerization initiator and a thermal polymerization accelerator. In this case, a cured product (molded article) can be obtained in the desired shape by effecting curing by polymerization inside a mold or on a steel belt. More specifically, all the common molding processes such as injection molding, extrusion molding, compression molding, transfer molding, calendar molding, and cast molding can be applied.

In the case where a cured product (molded article) is produced by photoirradiation, ultraviolet light with a wavelength of 100-400 nm or visible light with a wavelength of 400-700 nm is used to irradiate a curable resin composition. The wavelength of light is not specifically limited, but near ultraviolet light with a wavelength of 200-400 nm is used preferably. The lamps to serve as a power source for ultraviolet light include low-pressure mercury lamps (output: 0.4-4 W/cm), high-pressure mercury lamps (40-160 W/cm), ultrahigh-pressure mercury lamps (173-435 W/cm), metal halide lamps (80-160 W/cm), pulse xenon lamps (80-120 W/cm), and electrodeless discharge lamps (80-120 W/cm). As the mercury lamps respectively show characteristic spectral distribution, they are selected to suit the kind of photopolymerization initiator to be used.

Several processes are available for producing a cured product (molded article) by photoirradiation. According to one process, for example, a curable resin composition is injected into a mold that has a cavity of arbitrary shape and is constructed of a transparent material such as quartz glass, the curing of the composition is effected by irradiation with ultraviolet light using one of the aforementioned mercury lamps, and the cured product of the desired shape is released from the mold. According to another process that does not use a mold, a curable resin composition is applied, for example, to a moving steel belt using a doctor blade or a roll coater and cured by irradiation with one of the aforementioned mercury lamps to yield a molded article in the form of a sheet. Further, a process based on a combination of heating and photoirradiation may be used for the production of a molded article according to this invention.

Effects of the Invention

Application of the process for producing a curable cage-type silicone copolymer according to this invention enables one to control the molecular weight at will and perform material design to serve the purpose. That is, the condensation of a cage-type silsesquioxane compound containing an alkoxyl group or silanol group can give a copolymer in which a cage structure is incorporated in its main chain. A curable resin composition comprising the said copolymer yields a cured product of excellent transparency and heat resistance and the molded article thus obtained provides a transparent material which is lightweight and highly impact-resistant. The material can expand its area of use to optical applications such as lenses, optical disks, optical fibers, and base plates for flat panel displays, to a variety of transport machines, and to housing as substitute for glass in the window and is of high industrial utility.

Further, application of the process for producing a cage-type siloxane compound containing an alkoxyl group or silanol group according to this invention enables one to produce the said siloxane compound in which the content of the alkoxyl or silanol group per unit cage structure is adjusted and the structure is controlled to keep the molecular weight distribution low.

PREFERRED EMBODIMENTS OF THE INVENTION

This invention will be described with reference to the examples below.

The following abbreviations are used below; Me for a methyl group, Et for an ethyl group, and Ph for a phenyl group.

Synthetic Example 1

Synthesis of Alkoxyl-Containing Cage-type Siloxane Compound A

The following synthetic example uses the process described in Japan Tokkyo Koho No. Sho-40-15989 (1965) and relates to an example of the production of cage-type octaphenylsilsesquioxane with a structural unit represented by $(C_6H_5SO_{3/2})_8$. In a reaction vessel were placed 2,500 ml of toluene and 525 g of phenyltrichlorosilane and cooled to 0° C. A suitable amount of water was added dropwise and the mixture was stirred until hydrolysis was finished. The hydrolysis product was washed with water, 83 ml of a commercially available 30% benzyltrimethylammonium hydroxide solution was added, and the mixture was heated under reflux for 4 hours. Then, the whole mixture was cooled and left standing for approximately 96 hours. After the lapse of this time, the slurry formed was again heated under reflux for 24 hours, then cooled and filtered to give 375 g of octaphenylsilsesquioxane as a white powder.

Then, 1,000 ml of toluene, 1.23 g (13.5 millimoles) of tetramethylammonium hydroxide (4.9 g as a 25% methanol solution), 203 g (197 millimoles) of the octaphenylsilsesquioxane obtained above, and 51.2 g (197 millimoles) of 3-methacryloxypropyldiethoxymethylsilane were placed in a reaction vessel equipped with a Dean Stark trap and a cooling tube, the mixture was heated at 80° C. for 1 hour while distilling off methanol, then the mixture was heated up to 100° C., the temperature of the mixture was returned to room temperature after 2 hours, and the reaction was regarded as over. The white powder of octaphenylsilsesquioxane in the reaction solution disappeared and the reaction could be judged to have proceeded to completion. The reaction solution was neutralized with a 10% aqueous citric acid solution, washed with water, and dried over anhydrous magnesium sulfate. The magnesium sulfate was filtered off and the filtrate was concentrated to yield 197 g (78% yield) of alkoxyl-containing cage-type siloxane compound A as a colorless, transparent, and viscous liquid. The alkoxyl-containing cage-type siloxane compound A thus obtained was analyzed by GPC and NMR and confirmed to be represented by the following formula (7-1A)

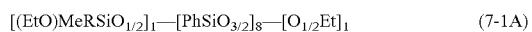

wherein R is a 3-methacryloxypropyl group.

Synthetic Example 2

Synthesis of Silanol-Containing Cage-Type Siloxane Compound A

In a reaction vessel equipped with a dropping funnel were placed 500 ml of 2-propanol, 350 ml of toluene, and 61.5 g (47.5 millimoles) of the alkoxyl-containing cage-type siloxane compound A (7-1A) obtained in the aforementioned Synthetic Example 1. To this reaction solution was added dropwise 1.4 g of 2% hydrochloric acid (1 millimole of HCl and 105 millimoles of $H_2O$) and the resulting solution was stirred at room temperature for 24 hours. The reaction solution was neutralized with an aqueous sodium hydrogen carbonate solution, washed with water, and dehydrated over anhydrous magnesium sulfate. The magnesium sulfate was filtered off and the filtrate was concentrated to yield 53.5 g (91% yield) of silanol-containing cage-type siloxane compound A as a colorless, transparent, and viscous liquid. The silanol-containing cage-type siloxane compound A thus obtained was analyzed by GPC and NMR and confirmed to be represented by the following formula (7-2A)

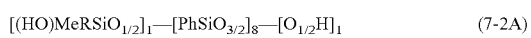

wherein R is a 3-methacryloxypropyl group.

Synthetic Example 3

Synthesis of Alkoxyl-Containing Cage-Type Siloxane Compound B

This synthetic example is based on the process laid open in JP2004-143449 A filed for application earlier and relates to an example of the production of a cage-type polyvinylsilsesquioxane with a structural unit represented by $(H_2C=CH-SiO_{3/2})_n$. In a reaction vessel were placed 750 ml of toluene, 425 ml of 2-propanol, and 186 g of a 5% aqueous solution of tetramethylammonium hydroxide (TMAH). To the solution in the reaction vessel was added dropwise a solution of 251 g of vinyltrimethoxysilane in 125 ml of toluene over 3 hours with stirring at room temperature. After completion of the dropwise addition, the solution was stirred at room temperature for 2 hours, then the stirring was stopped, and the solution was left standing for 1 day. The reaction solution was neutralized with a 10% aqueous citric acid solution, washed with a saturated aqueous sodium chloride solution, dehydrated over anhydrous magnesium sulfate, and concentrated to yield 103 g of the hydrolytic polycondensation product of vinyltrimethoxysilane.

Then, 1,100 g of the hydrolytic polycondensation product of vinyltrimethoxysilane obtained above, 2,000 ml of toluene, and 17.2 g of a 5% aqueous TMAH solution were placed in a reaction vessel equipped with a Dean Stark trap and a cooling tube and the mixture was heated under reflux at 120° C. for 3 hours while distilling off water. The mixture was cooled to room temperature, neutralized with a 10% aqueous citric acid solution, washed with a saturated aqueous sodium chloride solution, dehydrated over anhydrous magnesium sulfate, and concentrated to yield 97 g of cage-type polyvinylsilsesquioxane. The cage-type polyvinylsilsesquioxane thus obtained was analyzed by GPC and LC/APCI-MS (liquid chromatography/atmospheric pressure chemical ionization-mass spectrometry) and confirmed to be a mixture of cage-type vinylsiloxanes with a structural unit represented by $(H_2C=CH-SiO_{3/2})_n$ (wherein n is mainly 8, 10, 12, and 14 and is 10 on the average).

Thereafter, a modified charge stock consisting of 250 ml of toluene, 390 mg (4.3 millimoles) of tetramethylammonium hydroxide (1.55 g as a 25% methanol solution), 50.0 g of the mixture of cage-type vinylsiloxanes $(H_2C=CH-SiO_{3/2})_n$ obtained above (63 millimoles on the assumption that n=10 although n is mainly 8, 10, 12, and 14 and is 10 on the average), and 9.4 g (63 millimoles) of dimethyldimethoxysilane was processed according to the same procedure as the one in Synthetic Example 1 to yield 50.1 g (84% recovery) of alkoxyl-containing cage-type siloxane compound B as a colorless, transparent, and viscous liquid. This alkoxyl-containing cage-type siloxane compound B was analyzed by GPC and NMR and confirmed to be represented by the following formula (7-1B).

$$[(EtO)Me_2SiO_{1/2}]_1\text{—}[H_2C\text{⊚}CH\text{—}SiO_{3/2}]_{10}\text{—}[O_{1/2}Et]_1 \quad (7\text{-}1B)$$

Synthetic Example 4

Synthesis of Silanol-Containing Cage-Type Siloxane Compound B

In a reaction vessel equipped with a dropping funnel were placed 200 ml of 2-propanol, 170 ml of toluene, and 25.0 g (27 millimoles) of the alkoxyl-containing cage-type siloxane compound B obtained in Synthetic Example 3. To the resulting solution was added dropwise a mixture of 6.5 g (71.5 millimoles) of tetramethylammonium hydroxide (26 g as a 25% methanol solution), 1.5 g (83 millimoles) of deionized water, and 150 ml of 2-propanol and the reaction solution was stirred at room temperature for 3 hours. To the reaction solution was added 20 ml of toluene, the solution was stirred, neutralized with a 10% aqueous citric acid solution, washed with a saturated aqueous sodium chloride solution, dehydrated over anhydrous magnesium sulfate, and concentrated to yield 21.2 g (92% yield) of silanol-containing cage-type siloxane compound B. The silanol-containing cage-type siloxane compound B thus obtained was analyzed by GPC and NMR and confirmed to be represented by the following formula (7-2B).

$$[(HO)Me_2SiO_{1/2}]_1\text{—}[H_2C\text{=}CH\text{—}SiO_{3/2}]_{10}\text{—}[O_{1/2}H]_1 \quad (7\text{-}2B)$$

Synthetic Example 5

Synthesis of Alkoxyl-Containing Cage-Type Siloxane Compound a

Alkoxyl-containing cage-type siloxane compound a was synthesized by using cage-type octaphenylsilsesquioxane represented by $(C_6H_5SO_{3/2})_8$ as a cage-type siloxane compound and 3-methacryloxypropylmethyldiethoxysilane represented by $RMeSi(OEt)_2$ (wherein R is a 3-methacryloxypropyl group) as a dialkoxysilane in the following manner.

In a reaction vessel equipped with a Dean Stark trap and a cooling tube were placed 100 ml of toluene, 123 mg (1.35 millimoles) of tetramethylammonium hydroxide (0.49 g as a 25% methanol solution), 20.29 g (19.7 millimoles) of the octaphenylsilsesquioxane obtained in Synthetic Example 1, and 5.12 g (19.7 millimoles) of 3-methacryloxypropyldiethoxymethylsilane and the resulting solution was heated at 80° C. for 1 hour while distilling off methanol. The solution was then heated to 100° C., the temperature of the solution was returned to room temperature after 2 hours, and the reaction was regarded as over. The white powder of octaphenylsilsesquioxane in the reaction solution disappeared and the reaction was judged to have proceeded to completion. The reaction solution was neutralized with a 10% aqueous citric acid solution, washed with water, and dehydrated over anhydrous magnesium sulfate. The magnesium sulfate was filtered off and the filtrate was concentrated to yield 19.7 g (78% yield) of the target alkoxyl-containing cage-type siloxane compound a as a colorless, transparent, and viscous liquid.

The alkoxyl-containing cage-type siloxane compound a thus obtained showed a number average molecular weight $(M_n)$ of 1,212, a weight average molecular weight $(M_w)$ of 1,405, and a molecular weight distribution $(M_w/M_n)$ of 1.159 when analyzed by GPC. In analysis by 1H-NMR, the signal at 7-8 ppm assignable to 40 phenyl protons (40H) of octaphenylsilsesquioxane, the signal at 5.4 and 6.0 ppm assignable to 2 alkene protons (2H) of the methacryl group, and the signal at 3.7 ppm assignable to 2 methylene protons (2H) of the ethoxyl group were respectively integrated and the integrals were designated as S(Ph) (=40 in an arbitrary unit), S(M), and S(E). Then, the ratio of the integrals was found as follows; S(Ph):S(M):S(E)=40:1.9:3.8. This indicates that the alkoxyl-containing cage-type siloxane compound a thus obtained can be represented by the following formula (7.1a)

$$[(EtO)MeRSiO_{1/2}]_n\text{—}[PhSiO_{3/2}]_8\text{—}[O_{1/2}Et]_b \quad (7.1a)$$

wherein R is a 3-methacryloxypropyl group, a=0.95, and b=0.95. Furthermore, in analysis by LC/APCI-MS, a spectrum assignable to a fragment ion formed by addition of an ammonium ion to the compound represented by the aforementioned formula (7.1a) wherein a=1 and b=1 was detected at m/z=1,311.9. These findings indicate that alkoxyl-containing cage-type siloxane compound a consists of one molecule of cage-type octaphenylsilsesquioxane to which two methoxyl groups are added.

Synthetic Example 6

Synthesis of Silanol-Containing Cage-Type Siloxane Compound a-OH Using Alkoxyl-Containing Cage-Type Siloxane Compound A In a reaction vessel equipped with a dropping funnel were placed 10 ml of 2-propanol, 7 ml of toluene, and 1.23 g of the alkoxyl-containing cage-type siloxane compound a obtained in Synthetic Example 5 (0.95 millimole on the assumption that the molecular weight is 1,292 when a=1 and b=1 in formula (7.1a)). To the reaction solution was added dropwise 38 mg of 2% hydrochloric acid (0.02 millimole of HCl and 2.09 millimoles of $H_2O$) at room temperature and the reaction solution was stirred at room temperature for 24 hours. The reaction solution was neutralized with an aqueous sodium hydrogen carbonate solution, washed with water, and dehydrated over anhydrous magnesium sulfate. The magnesium sulfate was filtered off and the filtrate was concentrated to yield 1.07 g (91% yield) of the target silanol-containing cage-type siloxane compound a-OH The silanol-containing cage-type siloxane compound a-OH thus obtained showed a number average molecular weight $(M_n)$ of 1,165, a weight average molecular weight $(M_w)$ of 1,349, and a molecular weight distribution $(M_w/M_n)$ of 1.158 when analyzed by GPC. Analysis by 1H-NMR showed the absence of a signal assignable to the ethoxyl group and analysis by IR showed the presence of a broad peak near 3310 $cm^{-1}$ which is assignable to silanol. Furthermore, in analysis by LC/APCI-MS, a spectrum of a fragment ion formed by addition of a proton to the compound represented by the following formula (7.2a)

$$[(HO)MeRSiO_{1/2}]_n\text{—}[PhSiO_{3/2}]8\text{—}[O_{1/2}H]_b \quad (7.2a)$$

(wherein R is a methacryloxypropyl group, a=1, and b=1) was detected at m/z=1,238.8. These findings indicate that silanol-containing cage-type siloxane compound a-OH consists of one molecule of cage-type octaphenylsilsesquioxane to which two silanol groups are added.

Synthetic Example 7

Synthesis of Alkoxyl-Containing Cage-Type Siloxane Compound b

Alkoxyl-containing cage-type siloxane compound b was synthesized by using cage-type octaphenylsilsesquioxane represented by $(C_6H_5SO_{3/2})_8$ as a cage-type siloxane compound and vinylmethyldimethoxysilane represented by $RMeSi(OEt)_2$ (wherein R is a vinyl group) as a dialkoxysilane in the following manner.

A modified charge stock consisting of 50 ml of toluene, 60 mg (0.66 millimole) of tetramethylammonium hydroxide (0.24 g as a 25% methanol solution), 10.00 g (9.69 millimoles) of the octaphenylsilsesquioxane obtained in Synthetic Example 1, and 1.55 g (9.69 millimoles) of vinylmethyldimethoxysilane was processed according to the same procedure as the one in Synthetic Example 5 to yield 8.87 g (77% yield) of alkoxyl-containing cage-type siloxane compound b as a colorless, transparent, and viscous liquid.

The alkoxyl-containing cage-type siloxane compound b thus obtained showed a number average molecular weight ($M_n$) of 1,095, a weight average molecular weight ($M_w$) of 1,207, and a molecular weight distribution ($M_w/M_n$) of 1.159 when analyzed by GPC. In analysis by 1H-NMR, the signal at 7-8 ppm assignable to 40 phenyl protons (40H) of octaphenylsilsesquioxane, the signal near 5.9 ppm assignable to 3 protons (3H) of the vinyl group, and the signal at 3.7 ppm assignable to 2 methylene protons (2H) of the ethoxyl group were respectively integrated and the integrals were designated as S(Ph) (=40 in an arbitrary unit), S(M), and S(E). Then, the ratio of the integrals was found as follows; S(Ph): S(M):S(E)=40:2.9:3.8. This indicates that alkoxyl-containing cage-type siloxane compound b can be represented by the following formula (7.1b).

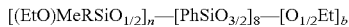  (7.1b)

wherein R is a vinyl group, a=0.97, and b=0.95.

Synthetic Example 8

Synthesis of Silanol-Containing Cage-Type Siloxane Compound b-OH Using Alkoxyl-Containing Cage-Type Siloxane Compound b The procedure same as the one in Synthetic Example 6 was followed with the exception of using 1.13 g of alkoxyl-containing cage-type siloxane compound b (0.95 millimoles on the assumption that the molecular weight is 1,192 when a=1 and b=1 in formula (7.1a)) in place of alkoxyl-containing cage-type siloxane compound a to yield 1.07 g (91% yield) of silanol-containing cage-type siloxane compound b-OH as a colorless, transparent, and viscous liquid. The silanol-containing cage-type siloxane compound b-OH thus obtained showed a number average molecular weight ($M_n$) of 1,147, a weight average molecular weight ($M_w$) of 1,255, and a molecular weight distribution ($M_w/M_n$) of 1.094 when analyzed by GPC. Analysis by 1H-NMR showed the absence of a signal assignable to the ethoxyl group and analysis by IR showed the presence of a broad peak near 3310 cm$^{-1}$ which is assignable to silanol. These findings indicate that silanol-containing cage-type siloxane compound b-OH consists of alkoxyl-containing cage-type siloxane compound b whose alkoxyl group is converted to the silanol group.

Synthetic Example 9

Synthesis of Alkoxyl-Containing Cage-Type Siloxane Compound c

Alkoxyl-containing cage-type siloxane compound c was synthesized by using the mixture of cage-type polyvinylsilsesquioxanes $(H_2C=CH—SiO_{3/2})_n$ (wherein n is mainly 8, 10, 12, and 14 and is 10 on the average) obtained in Synthetic Example 3 as a cage-type siloxane compound and dimethyldiethoxysilane $Me_2Si(OEt)_2$ as a dialkoxysilane in the following manner.

A modified charge stock consisting of 50 ml of toluene, 78 mg (0.86 millimole) of tetramethylammonium hydroxide (0.31 g as a 25% methanol solution), 10.00 g of the mixture of cage-type vinylsiloxanes $(H_2C=CH—SiO_{3/2})_n$ obtained in Synthetic Example 3 (12.7 millimoles on the assumption that n=10 although n is mainly 8, 10, 12, and 14 and is 10 on the average), and 1.88 g (12.7 millimoles) of dimethyldimethoxysilane was processed according to the same procedure as the one in Synthetic Example 5 to yield 10.01 g (84% recovery) of alkoxyl-containing cage-type siloxane compound c as a colorless, transparent, and viscous liquid.

The alkoxyl-containing cage-type siloxane compound c thus obtained showed a number average molecular weight ($M_n$) of 986, a weight average molecular weight ($M_w$) of 1,315, and a molecular weight distribution ($M_w/M_n$) of 1.334 when analyzed by GPC. In analysis by 1H-NMR, the signal at 5.8-6.2 ppm assignable to 30 protons (30H) of the vinyl group of cage-type vinylsiloxane, the signal near 0.1 ppm assignable to 3 protons (3H) of the methyl group, and the signal at 3.7 ppm assignable to 2 methylene protons (2H) of the ethoxyl group were respectively integrated and the integrals were designated as S(cV) (=30 in an arbitrary unit), S(Me), and S(E). Then, the ratio of the integrals was found as follows; S(cV):S(Me):S(E)=30:6:3.9. This indicates that alkoxyl-containing cage-type siloxane compound c can be represented by the following formula (7.1c).

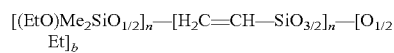  (7.1c)

wherein n=10, a=1.00, and b=0.95.

Synthetic Example 10

Synthesis of Silanol-Containing Cage-Type Siloxane Compound c-OH Using Alkoxyl-Containing Cage-Type Siloxane Compound c In a reaction vessel equipped with a dropping funnel were placed 10 ml of 2-propanol, 7 ml of toluene, and 1.0 g (1.36 millimoles when the molecular weight calculated for the case of a=1 and b=1 in formula (7.1c) is 734) of alkoxyl-containing cage-type siloxane compound c. To this reaction solution was added dropwise a mixture of 260 mg (2.86 millimoles) of tetramethylammonium hydroxide (1.04 g as a 25% methanol solution), 59 mg (3.27 millimoles) of deionized water, and 6 ml of 2-propanol and the solution was stirred at room temperature for 3 hours. To the reaction solution was added 20 ml of toluene, the stirring was continued, the solution was neutralized with a 10% aqueous citric acid solution, washed with a saturated aqueous sodium chloride solution, dehydrated over anhydrous magnesium sulfate, and concentrated to yield 6.2 g (92% yield) of silanol-containing cage-type siloxane compound c-OH.

The silanol-containing cage-type siloxane compound c-OH thus obtained showed a number average molecular weight ($M_n$) of 577, a weight average molecular weight ($M_w$) of 641, and a molecular weight distribution ($M_w/M_n$) of 1.111 when analyzed by GPC. Analysis by 1H-NMR showed the absence of a signal assignable to the ethoxyl group and analysis by IR showed the presence of a broad peak near 3310 cm$^{-1}$ which is assignable to silanol. These findings indicate that silanol-containing cage-type siloxane compound c-OH consists of alkoxyl-containing cage-type siloxane compound c whose alkoxyl group is converted to the silanol group.

Synthetic Example 11

Synthesis of Alkoxyl-Containing Cage-Type Siloxane Compound d

Alkoxyl-containing cage-type siloxane compound d was synthesized by using the mixture of cage-type polyvinylsilsesquioxanes ($H_2C=CH—SiO_{3/2})_n$ obtained in Synthetic Example 3 (wherein n is mainly 8, 10, 12, and 14 and is 10 on the average) as a cage-type siloxane compound and 3-methacryloxypropylmethyldiethoxysilane RMeSi(OEt)$_2$ (wherein R is a 3-methacryloxypropyl group) as a dialkoxysilane in the following manner.

A modified charge stock consisting of 50 ml of toluene, 78 mg (0.86 millimole) of tetramethylammonium hydroxide (0.31 g as a 25% methanol solution), 10.00 g of the mixture of cage-type vinylsiloxanes ($H_2C=CH—SiO_{3/2})_n$ (wherein n is mainly 8, 10, 12, and 14 and is 10 on the average; the amount added is calculated to be 12.7 millimoles when n=10) obtained in Synthetic Example 3, and 3.30 g (12.7 millimoles) of 3-methacryloxypropylmethyldiethoxysilane was processed according to the same procedure as the one in Synthetic Example 5 to yield 11.84 g (89% recovery) of alkoxyl-containing cage-type siloxane compound d as a colorless, transparent, and viscous liquid.

The alkoxyl-containing cage-type siloxane compound d thus obtained showed a number average molecular weight ($M_n$) of 1,110, a weight average molecular weight ($M_w$) of 1,521, and a molecular weight distribution ($M_w/M_n$) of 1.370 when analyzed by GPC. In analysis by 1H-NMR, the signal at 5.8-6.2 ppm assignable to both 30 protons (30H) of the vinyl group of cage-type vinylsiloxane and one prone (1H) of 2 alkene protons of the methacryl group, the signal at 5.5 ppm assignable to the remaining one proton (1H) of the methacryl group, and the signal at 3.7 ppm assignable to 2 methylene protons (2H) of the ethoxyl group were respectively integrated and the integrals were designated as S(cV+M) (=31 in an arbitrary unit), S(M), and S(E). Then, the ratio of the integrals was found as follows; S(cV+M):S(M):S(E)=31:0.89:3.8. This indicates that alkoxyl-containing cage-type siloxane compound d can be represented by the following formula (7.1d).

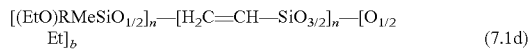  (7.1d)

wherein R is a methacryloxypropyl group, n=10, a=0.89, and b=1.01.

Synthetic Example 12

Synthesis of Alkoxyl-Containing Cage-Type Siloxane Compound d-OH Using Alkoxyl-Containing Cage-Type Siloxane Compound d Using 1.43 g of the alkoxyl-containing cage-type siloxane compound d synthesized in Synthetic Example 11 (1.36 millimoles on the assumption that the molecular weight is 1,050 when a=1 and b=1 in formula (7.1d)) in place of 1.0 g of alkoxyl-containing cage-type siloxane compound c, the same procedure as the one in Synthetic Example 10 was followed to yield 0.91 g (92% yield) of silanol-containing cage-type siloxane compound d-OH.

The silanol-containing cage-type siloxane compound d-OH thus obtained showed a number average molecular weight ($M_n$) of 1,283, a weight average molecular weight ($M_w$) of 1,511, and a molecular weight distribution ($M_w/M_n$) of 1.178 when analyzed by GPC. Analysis by 1H-NMR showed the absence of a signal assignable to the ethoxyl group and analysis by IR showed the presence of a broad peak near 3310 cm$^{-1}$ which is assignable to silanol. These findings indicate that silanol-containing cage-type siloxane compound d-OH is said to consist of alkoxyl-containing cage-type siloxane compound d whose alkoxyl group is converted to the silanol group.

Synthetic Example 13

Synthesis of Alkoxyl-Containing Cage-Type Siloxane Compound e

Using the mixture of cage-type polyvinylsilsesquioxanes ($H_2C=CH—SiO_{3/2})_n$ obtained in Synthetic Example 3 (wherein n is mainly 8, 19, 12, and 14 and is 10 on the average) as a cage-type siloxane compound and 3-glycidoxypropylmethyldiethoxysilane RMeSi(OEt)$_2$ (wherein R is a 3-glycidoxypropyl group) as a dialkoxysilane, alkoxyl-containing cage-type siloxane compound e was synthesized in the following manner.

A modified charge stock consisting of 50 ml of toluene, 78 mg (0.86 millimole) of tetramethylammonium hydroxide (0.31 g as a 25% methanol solution), 10.00 g of the mixture of cage-type vinylsiloxanes ($H_2C=CH—SiO_{3/2})_n$ obtained in Synthetic Example 3 (12.7 millimoles on the assumption that n=10 although n is mainly 8, 10, 12, and 14 and is 10 on the average), and 3.15 g (12.7 millimoles) of 3-glycidoxypropylmethyldiethoxysilane was processed according to the same procedure as the one in Synthetic Example 5 to yield 11.17 g (85% recovery) of alkoxyl-containing cage-type siloxane compound e as a colorless, transparent, and viscous liquid.

The alkoxyl-containing cage-type siloxane compound e thus obtained showed a number average molecular weight ($M_n$) of 1,138, a weight average molecular weight ($M_w$) of 1,578, and a molecular weight distribution ($M_w/M_n$) of 1.387 when analyzed by GPC. In analysis by 1H-NMR, the signal at 5.8-6.2 ppm assignable to 30 protons (30H) of the vinyl group of cage-type vinylsiloxane, the signal at 2.45 and 2.6 ppm assignable to 2 protons (2H) of the glycidyl group, and the signal at 1.2 ppm assignable to 3 methyl protons (3H) of the ethoxyl group were respectively integrated and the integrals were designated as S(cV) (=30 in an arbitrary unit), S(G), and S(E). Then the ratio of the integrals was found as follows; S(cV):S(G):S(E)=30:1.99:5.98. This indicates that alkoxyl-containing cage-type siloxane compound e can be represented by the following formula (7.1e).

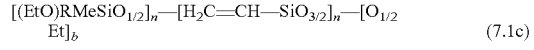  (7.1c)

wherein R is a 3-glycidoxypropyl group, n=10, a=1.00, and b=1.00.

Synthetic Example 14

Synthesis of Silanol-Containing Cage-Type Siloxane Compound e-OH Using Alkoxyl-Containing Cage-Type Siloxane Compound e Using 1.41 g of the alkoxyl-containing cage-type siloxane compound e obtained in Synthetic Example 13 (1.36 millimoles on the assumption that the molecular weight is 1,038 when a=1 and b=1 in formula (7.1e)) in place of 1.0 g of alkoxyl-containing cage-type siloxane compound c, the same procedure as the one in Synthetic Example 10 was followed to yield 0.86 g (88% yield) of silanol-containing cage-type siloxane compound e-OH.

The silanol-containing cage-type siloxane compound d-OH thus obtained showed a number average molecular weight ($M_n$) of 1,220, a weight average molecular weight ($M_w$) of 1,579, and a molecular weight distribution ($M_w/M_n$) of 1.294 when analyzed by GPC. Analysis by 1H-NMR showed the absence of a signal assignable to the ethoxyl group and analysis by IR showed the presence of a broad peak near 3310 cm$^{-1}$ which is assignable to silanol. These findings indicate that silanol-containing cage-type siloxane compound e-OH consists of alkoxyl-containing cage-type siloxane compound e whose alkoxyl group is converted to the silanol group.

Synthetic Example 15

Using a mixture of 25.2 g (0.17 mole) of trimethoxyethylsilane and 25.5 g (0.17 mole) of trimethoxyvinylsilane in place of 50.3 g (0.34 mole) of trimethoxyvinylsilane, the same procedure as the one in Synthetic Example 3 was followed to yield cage-type poly(vinyl-ethyl)silsesquioxane. When analyzed as in Synthetic Example 3, the said compound was found to be a mixture of poly(vinyl-ethyl)siloxanes represented by $[R^1SiO_{3/2}]_n$ wherein n is mainly 8, 10, 12, and 14, $R^1$ consists of a vinyl group and an ethyl group, and n is 10 on the average.

Synthetic Example 16

Synthesis of Alkoxyl-Containing Cage-Type Siloxane Compound f

Using the mixture of cage-type poly(vinyl-ethyl)siloxanes $[RiSiO_{3/2}]_n$ (wherein n is mainly 8, 10, 12, and 14 and is 10 on the average) obtained in Synthetic Example 15 as a cage-type siloxane compound and 3-methacryloxypropylmethyldiethoxysilane RMeSi(OEt)$_2$ (wherein R is a 3-methacryloxypropyl group) as a dialkoxysilane, alkoxyl-containing cage-type siloxane compound f was synthesized in the following manner.

A modified charge stock consisting of 50 ml of toluene, 78 mg (0.86 millimole) of tetramethylammonium hydroxide (0.31 g as a 25% methanol solution), 10.00 g of the mixture of cage-type vinylsiloxanes $[R^1SiO_{3/2}]_n$ obtained in Synthetic Example 15 (12.7 millimoles on the assumption that $R^1$ consists of an equal number of a vinyl group and an ethyl group and n=10 although n is mainly 8, 10, 12, and 14 and is 10 on the average), and 3.30 g (12.7 millimoles) of 3-methacryloxypropylmethyldiethoxysilane was processed as in Synthetic Example 5 to yield 12.64 g (95% recovery) of alkoxyl-containing cage-type siloxane compound f as a colorless, transparent, and viscous liquid.

The alkoxyl-containing cage-type siloxane compound f thus obtained showed a number average molecular weight ($M_n$) of 1,176, a weight average molecular weight ($M_w$) of 1,543, and a molecular weight distribution ($M_w/M_n$) of 1.312 when analyzed by GPC. In analysis by 1H-NMR, the signal at 0.6 ppm assignable to 10 methylene protons (10H, on the assumption that $R^1$ consists of an equal number of a vinyl group and an ethyl group and n=10) of the ethyl group of a mixture of cage-type poly(vinyl-ethyl)siloxanes, the signal at 5.5 ppm assignable to 1 alkene proton (1H) of the methacryl group, and the signal at 3.7 ppm assignable to 2 methylene protons (2H) of the ethoxyl group were respectively integrated and the integrals were designated as S(cEt) (=10 in an arbitrary unit), S(M), and S(E). Then, the ratio of the integrals was found as follows; S(cEt):S(M):S(E)=10:1.01:4.00. This indicates that alkoxyl-containing cage-type siloxane compound f can be represented by the following formula (7.1f).

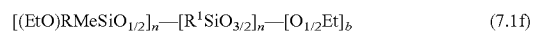

$$[(EtO)RMeSiO_{1/2}]_a - [R^1SiO_{3/2}]_n - [O_{1/2}Et]_b \qquad (7.1f)$$

wherein R is a 3-methacryloxypropyl group, $R^1$ consists of an equal number of a vinyl group and an ethyl group, n=10, a=1.01, and b=0.99.

Synthetic Example 17

Synthesis of Silanol-Containing Cage-Type Siloxane Compound f-OH Using Alkoxyl-Containing Cage-Type Siloxane Compound f Using 1.41 g of the alkoxyl-containing cage-type siloxane compound f obtained in Synthetic Example 16 (1.36 millimoles on the assumption that the molecular weight is 1,045 when R is a methacryloxypropyl group, $R^1$ consists of an equal number of a vinyl group and an ethyl group, a=1, and b=1 in formula (7.1f) in place of 1.0 g of alkoxyl-containing cage-type siloxane compound c, the same procedure as the one in Synthetic Example 10 was followed to yield 0.89 g (90% yield) of silanol-containing cage-type siloxane compound f-OH.

The silanol-containing cage-type siloxane compound d-OH thus obtained showed a number average molecular weight ($M_n$) of 1,150, a weight average molecular weight ($M_w$) of 1,520, and a molecular weight distribution ($M_w/M_n$) of 1.322 when analyzed by GPC. Analysis by 1H-NMR showed the absence of a signal assignable to the ethoxyl group and analysis by IR showed the presence of a broad peak near 3310 cm$^{-1}$ which is assignable to silanol. These findings indicate that silanol-containing cage-type siloxane compound f-OH consists of alkoxyl-containing cage-type siloxane compound f whose alkoxyl group is converted to the silanol group.

Example 1

In a reaction vessel equipped with a dropping funnel and a cooling tube were placed 15 ml of toluene, 9.0 g of (7 millimoles) of the alkoxyl-containing cage-type siloxane compound A (formula 7-1A) obtained in the aforementioned Synthetic Example 1, and 4 mg (0.044 millimole) of tetramethylammonium hydroxide (153 mg as a 2.5% methanol solution) in an atmosphere of nitrogen. While stirring the reaction solution at 70° C., 4.6 g of silanol-terminated polydimethylsiloxane (DMS-S12 with a number average molecular weight ($M_n$) of 400-700, available from AZmax Co., Ltd.) was added dropwise over 3 hours to the solution from the dropping funnel. The reaction solution was stirred further for 3 hours, cooled to room temperature, neutralized with a 10% aqueous citric acid solution, washed with water, and dehydrated over anhydrous magnesium sulfate. The magnesium sulfate was filtered off and the filtrate was concentrated to yield 12.5 g of curable cage-type silicone copolymer A as a colorless, transparent, and viscous liquid. The curable cage-type silicone copolymer A thus obtained showed a weight average molecular weight ($M_w$) of 96,768 when analyzed by GPC. The signals assignable to phenyl, methyl, ethoxyl, and 3-methacryloxypropyl groups were observed in analysis by 1H-NMR. Hence, it was confirmed that the aforementioned curable cage-type silicone copolymer A is represented by general formula (1-1) wherein $R^1$ is a phenyl group, $R^2$ consists of a methyl group and a 3-methacryloxypropyl group at a ratio of 1:1, a=1, b=1, n=8, and m=52.5. Furthermore, regarding Z in general formula (1-1), $R^3$ is a methyl group and p=7.2 in general formula (2) shown earlier. Regarding $Y^1$, $R^1$ is a phenyl group, $R^2$ consists of a methyl group and a 3-methacryloxypropyl group at a ratio of 1:1, a=1, b=1, n=8, and an ethyl group and a hydrogen atom are selected for $R^4$ in general formula (3), (4), or (5)

Example 2

In a reaction vessel equipped with a dropping funnel and a cooling tube were placed 15 ml of toluene, 1.2 g (8 millimoles) of dimethyldiethoxysilane, and 4 mg (0.044 millimole) of tetramethylammonium hydroxide (153 mg as a 2.5% methanol solution) in an atmosphere of nitrogen. While stirring the reaction solution at 70° C., a solution of 8.6 g (7 millimoles) of the silanol-containing cage-type siloxane compound A (formula 7-2A) obtained in the aforementioned Synthetic Example 2 in 5 ml of toluene was added dropwise over 3 hours to the solution from the dropping funnel. The reaction solution was stirred further for 3 hours, cooled to room temperature, neutralized with a 10% aqueous citric acid solution, washed with water, and dehydrated over anhydrous magnesium sulfate. The magnesium sulfate was filtered off and the filtrate was concentrated to yield 9.0 g of curable cage-type silicone copolymer B as a colorless, transparent, and viscous liquid. The curable cage-type silicone copolymer B thus obtained showed a weight average molecular weight ($M_w$) of 16,708 when analyzed by GPC. The signals assignable to phenyl, methyl, ethoxyl, and 3-methacryloxypropyl groups were observed in analysis by 1H-NMR. Hence, it was confirmed that the aforementioned curable cage-type silicone copolymer B is represented by general formula (1-1) wherein $R^1$ is a phenyl group, $R^2$ consists of a methyl group and a 3-methacryloxypropyl group at a ratio of 1:1, a=1, b=1, n=8, and m=12.7. Furthermore, regarding Z in general formula (1-1), $R^3$ is a methyl group and p=1.1 in general formula (2) shown earlier. Regarding $Y^1$, $R^1$ is a phenyl group, $R^2$ consists of a methyl group and a 3-methacryloxypropyl group at a ratio of 1:1, a=1, b=1, n=8, and an ethyl group and a hydrogen atom are selected for $R^4$ in general formula (3), (4), or (5).

Example 3

In a reaction vessel equipped with a dropping funnel and a cooling tube were placed 15 ml of toluene, 2.3 g of hydrogen-terminated polydimethylsiloxane (DMS-H03 with an $M_n$ of 400-500, available from AZmax Co., Ltd.), and 364 mg (4.1 millimoles) of N,N-diethylhydroxylamine in an atmosphere of nitrogen. While stirring the reaction solution, a solution of 6.3 g (5 millimoles) of the silanol-containing cage-type siloxane compound A (formula 7-2A) obtained in the aforementioned Synthetic Example 2 in 5 ml of toluene was added dropwise over 1 hour to the solution from the dropping funnel. The reaction solution was stirred further for 3 hours at 50° C., cooled to room temperature, neutralized with a 10% aqueous citric acid solution, washed with water, and dehydrated over anhydrous magnesium sulfate. The magnesium sulfate was filtered off and the filtrate was concentrated to yield 8.1 g of curable cage-type silicone copolymer C as a colorless, transparent, and viscous liquid. The curable cage-type silicone copolymer C thus obtained showed a weight average molecular weight ($M_w$) of 45,213 when analyzed by GPC. The signals assignable to phenyl, methyl, and 3-methacryloxypropyl groups were observed in analysis by 1H-NMR. Hence, it was confirmed that the aforementioned curable cage-type silicone copolymer C is represented by general formula (1-1) wherein $R^1$ is a phenyl group, $R^2$ consists of a methyl group and a 3-methacryloxypropyl group at a ratio of 1:1, a=1, b=1, n=8, and m=26.8. Furthermore, regarding Z in general formula (1-1), $R^3$ is a methyl group and p=6.1 in general formula (2) shown earlier. Regarding. $Y^1$, $R^1$ is a phenyl group, $R^2$ consists of a methyl group and a 3-methacryloxypropyl group at a ratio of 1:1, a=1, b=1, n=8, and $R^4$ is a hydrogen atom in general formula (3), (4), or (5).

Example 4

In a reaction vessel equipped with a dropping funnel and a cooling tube were placed 1.96 g (17 millimoles) of methyldichlorosilane and 16 ml of pyridine in an atmosphere of nitrogen. While stirring the reaction solution, a solution of 10.5 g (8.5 millimoles) of the silanol-containing cage-type siloxane compound A (formula 7-2A) obtained in the aforementioned Synthetic Example 2 in 77 ml of pyridine was added dropwise over 1 hour to the solution from the dropping funnel. The reaction solution was stirred further for 3 hours at 50° C., then cooled to room temperature, 100 ml of toluene and 50 ml of water were added to the solution, and the mixture was separated into an organic layer and an aqueous layer. The organic layer was taken out, washed three times with distilled water, then twice with a saturated aqueous sodium chloride solution, and dehydrated over anhydrous magnesium sulfate. The magnesium sulfate was filtered off and the filtrate was concentrated to yield 10.4 g of curable cage-type silicone copolymer D as a colorless, transparent, and viscous liquid. The curable cage-type silicone copolymer D thus obtained showed a weight average molecular weight ($M_w$) of 19,228 when analyzed by GPC. The signals assignable to phenyl, methyl, and 3-methacryloxypropyl groups were observed in analysis by 1H-NMR. Hence, it was confirmed that the aforementioned curable cage-type silicone copolymer D is represented by general formula (1-1) wherein R' is a phenyl group, $R^2$ consists of a methyl group and a 3-methacryloxypropyl group at a ratio of 1:1, a=1, b=1, n=8, and m=13.9. Furthermore, regarding Z in general formula (1-1), $R^3$ consists of a methyl group and a hydrogen atom at a ratio of 1:1 and p=2 in general formula (2) shown earlier. Regarding $Y^1$, $R^1$ is a phenyl group, $R^2$ consists of a methyl group and a 3-methacryloxypropyl group at a ratio of 1:1, a=1, b=1, n=8, and $R^4$ is a hydrogen atom in general formula (3), (4), or (5).

Example 5

In a reaction vessel equipped with a dropping funnel and a cooling tube were placed 5.0 g of the curable cage-type silicone copolymer D obtained in the aforementioned Synthetic Example 4 and 16 ml of pyridine in an atmosphere of nitrogen. While stirring the reaction solution, a solution of 5.0 g (42 millimoles) of dimethylvinylchlorosilane in 20 ml of THF was added dropwise at room temperature over 30 minutes to the solution from the dropping funnel. The reaction solution was stirred for 2 hours, then 30 ml of toluene and 30 ml of distilled water were added to the solution, and the mixture was separated into an organic layer and an aqueous layer. The organic layer was taken out, washed three times with distilled water, then twice with a saturated aqueous sodium chloride solution, and dehydrated over anhydrous magnesium sulfate. The magnesium sulfate was filtered off and the filtrate was concentrated to yield 4.8 g of curable cage-type silicone copolymer E as a colorless, transparent, and viscous liquid.

The curable cage-type silicone copolymer E thus obtained showed a weight average molecular weight ($M_w$) of 19,538 when analyzed by GPC. The signals assignable to phenyl, methyl, and 3-methacryloxypropyl groups were observed in analysis by 1H-NMR. Hence, it was confirmed that the aforementioned curable cage-type silicone copolymer E is represented by general formula (1-2) wherein $R^1$ is a phenyl group, $R^2$ consists of a methyl group and a 3-methacryloxypropyl group at a ratio of 1:1, a=1, b=1, n=8, and m=139. Furthermore, regarding Z in general formula (1-2), $R^3$ is a methyl group and p=2 in general formula (2) shown earlier. Regarding $Y^2$, $R^2$ in general formula (6) consists of a methyl group and a vinyl group at a ratio of 2:1.

Example 6

In a reaction vessel equipped with a dropping funnel and a cooling tube were placed 15 ml of toluene, 9.4 g (10 millimoles) of the alkoxyl-containing cage-type siloxane compound B (formula 7-1B) obtained in the aforementioned Synthetic Example 3, and 4 mg (0.044 millimoles) of tetramethylammonium hydroxide (153 mg as a 2.5% methanol solution) in an atmosphere of nitrogen. While stirring the reaction solution at 70° C., 4.6 g of silanol-terminated polydimethylsiloxane (DMS-S12 with a weight average molecular weight ($M_w$) of 400-700, available from AZmax Co., Ltd.) was added dropwise over 3 hours to the solution from the dropping funnel. The reaction solution was stirred further for 3 hours, cooled to room temperature, neutralized with a 10% aqueous citric acid solution, washed with water, and dehydrated over anhydrous magnesium sulfate. The magnesium sulfate was filtered off and the filtrate was concentrated to yield 12.3 g of curable cage-type silicone copolymer F as a colorless, transparent, and viscous liquid. The curable cage-type silicone copolymer F thus obtained showed a weight average molecular weight ($M_w$) of 45,634 when analyzed by GPC. The signals assignable to methyl, ethoxyl, and vinyl groups were observed in analysis by 1H-NMR. Hence, it was confirmed that the aforementioned curable cage-type silicone copolymer F is represented by general formula (1-1) wherein $R^1$ is a vinyl group, $R^2$ is a methyl group, a=1, b=1, n=10, and m=34.5. Furthermore, regarding Z in general formula (1-1), $R^3$ is a methyl group and p=7.2 in general formula (2) shown earlier. Regarding $Y^1$, $R^1$ is a vinyl group, $R^2$ is a methyl group, a=1, b=1, n=8, and an ethyl group and a hydrogen atom are selected for $R^4$ in general formula (3), (4), or (5).

Example 7

In a reaction vessel equipped with a dropping funnel and a cooling tube were placed 2.2 g (17 millimoles) of dimethyldichlorosilane and 16 ml of pyridine in an atmosphere of nitrogen. While stirring the reaction solution, a solution of 7.5 g (8.5 millimoles) of the silanol-containing cage-type siloxane compound B (formula 7-2B) obtained in the aforementioned Synthetic Example 4 in 77 ml of pyridine was added dropwise over 1 hour to the solution from the dropping funnel and the solution was stirred further for 3 hours at 50° C. The reaction solution was then cooled to room temperature, a solution of 4.3 g (40 millimoles) of trimethylchlorosilane in 20 ml of pyridine was newly added dropwise at room temperature over 30 minutes, and the solution was stirred for 2 hours. After the 2-hour stirring, 100 ml of toluene and 30 ml of distilled water were added to the solution and the mixture was separated into an organic layer and an aqueous layer. The organic layer was taken out, washed three times with distilled water, then twice with a saturated aqueous sodium chloride solution, and dehydrated over anhydrous magnesium sulfate. The magnesium sulfate was filtered off and the filtrate was concentrated to yield 7.1 g of curable cage-type silicone copolymer G as a colorless, transparent, and viscous liquid. The curable cage-type silicone copolymer G thus obtained showed a weight average molecular weight ($M_w$) of 36,098 when analyzed by GPC. The signals assignable to vinyl and methyl groups were observed in analysis by 1H-NMR. Hence, it was confirmed that curable cage-type silicone copolymer G is represented by general formula (1-2) wherein $R^1$ is a vinyl group, $R^2$ is a methyl group, a=1, b=1, n=10, and m=35. Furthermore, regarding Z in general formula (1-2), $R^3$ is a methyl group and p=2 in general formula (2) shown earlier. Regarding $Y^2$, $R^1$ is a methyl group in general formula (6).

Example 8

A transparent curable resin composition was obtained by mixing 100 parts by weight of the curable cage-type silicone copolymer A obtained in the aforementioned Example 1 and 1.0 part by weight of 1-hydroxycyclohexyl phenyl ketone (Irgacure 184, manufactured by Ciba Specialty Chemicals) as a photopolymerization initiator.

The curable resin composition obtained above was cast to a thickness of 0.4 mm using a roll coater and cured by irradiating with a high-pressure mercury lamp (output, 30 W/cm) at an integrated exposure dose of 2,000 mJ/cm$^2$ to yield a molded article in the form of a sheet with a prescribed thickness.

Example 9

A transparent curable resin composition was obtained by mixing 100 parts by weight of the curable cage-type silicone copolymer B obtained in the aforementioned Example 2 and 5.0 parts by weight of dicumyl peroxide (Percumyl D, manufactured by NOF Corporation) as a thermal polymerization initiator.

The curable resin composition obtained above was cast to a thickness of 0.4 mm using a roll coater, cured by irradiating with a high-pressure mercury lamp (output, 30 W/cm) at an integrated exposure dose of 2,000 mJ/cm$^2$, then heated in steps at 140° C. for 1 hour and at 180° C. for 1 hour to yield a molded article in the form of a sheet with a prescribed thickness.

Example 10

A transparent curable resin composition was obtained by mixing 100 parts by weight of the curable cage-type silicone copolymer C obtained in the aforementioned Example 3, 50 parts by weight of 1,3-bis(3-methacryloxypropyl)-1,1,3,3-tetramethydisiloxane, 1.5 parts by weight of 1-hydroxycyclohexyl phenyl ketone (Irgacure 184, manufactured by Ciba Specialty Chemicals) as a photopolymerization initiator, and 5.0 parts by weight of dicumyl peroxide (Percumyl D, manufactured by NOF Corporation) as a thermal polymerization initiator.

The curable resin composition obtained above was cast to a thickness of 0.4 mm using a roll coater, cured by irradiating with a high-pressure mercury lamp (output, 30 W/cm) at an integrated exposure dose of 2,000 mJ/cm$^2$, then heated in steps at 140° C. for 1 hour and at 180° C. for 1 hour to yield a molded article in the form of a sheet with a prescribed thickness.

Example 11

A transparent curable resin composition was obtained by mixing 100 parts by weight of the curable cage-type silicone copolymer D obtained in the aforementioned Example 4, 10 parts by weight of 1,3,5,7-tetramethyl-1,3,5,7-tetravinylcyclotetrasiloxane, 0.5 part by weight of a platinum-vinylsiloxane complex (SIP6830.3, manufactured by AZmax Co., Ltd.), and 1.5 parts by weight of 1-hydroxycyclohexyl phenyl ketone (Irgacure 184, manufactured by Ciba Specialty Chemicals) as a photopolymerization initiator.

The curable resin composition obtained above was cast to a thickness of 0.4 mm using a roll coater, heated at 80° C. for 1 hour, and then cured by irradiating with a high-pressure mercury lamp (output, 30 W/cm) at an integrated exposure dose of 2,000 mJ/cm$^2$ to yield a molded article in the form of a sheet with a prescribed thickness.

Example 12

A transparent curable resin composition was obtained by mixing 100 parts by weight of the curable cage-type silicone copolymer E obtained in the aforementioned Example 5, 20 parts by weight of 1,3,5,7-tetramethyl-1,3,5,7-tetravinylcyclotetrasiloxane, 0.5 part by weight of a platinum-vinylsiloxane complex (SIP6830.3, manufactured by AZmax Co., Ltd.), 1.5 parts by weight of 1-hydroxycyclohexyl phenyl ketone (Irgacure 184, manufactured by Ciba Specialty Chemicals) as a photopolymerization initiator, and 5.0 parts by weight of dicumyl peroxide (Percumyl D, manufactured by NOF Corporation) as a thermal polymerization initiator.

The curable resin composition obtained above was cast to a thickness of 0.4 mm using a roll coater, cured by irradiating with a high-pressure mercury lamp (output, 30 W/cm) at an integrated exposure dose of 2,000 mJ/cm$^2$, then heated in steps at 100° C. for 1 hour, at 140° C. for 1 hour, and at 180° C. for 1 hour to yield a molded article in the form of a sheet with a prescribed thickness.

Example 13

A transparent curable resin composition was obtained by mixing 100 parts by weight of the curable cage-type silicone copolymer F obtained in the aforementioned Example 6 and 10 parts by weight of dicumyl peroxide (Percumyl D, manufactured by NOF Corporation) as a thermal polymerization initiator.

The curable resin composition obtained above was cast to a thickness of 0.4 mm using a roll coater and heated in steps at 1001 for 1 hour, at 140° C. for 1 hour, and at 180° C. for 1 hour to yield a molded article in the form of a sheet with a prescribed thickness.

Example 14

A transparent curable resin composition was obtained by mixing 100 parts by weight of the curable cage-type silicone copolymer G obtained in the aforementioned Example 7, 160 parts by weight of 1,3,5,7-tetramethylcyclotetrasiloxane, and 1.5 parts by weight of a platinum-vinylsiloxane complex (SIP6830.3, manufactured by AZmax Co., Ltd.).

The curable resin composition obtained above was cast to a thickness of 0.4 mm using a roll coater and heated in steps at 100° C. for 1 hour, at 140° C. for 1 hour, and at 180° C. for 1 hour to yield a molded article in the form of a sheet with a prescribed thickness.

Example 15

A transparent curable resin composition was obtained by mixing 100 parts by weight of the curable cage-type silicone copolymer G obtained in the aforementioned Example 7, 100 parts by weight of 1,3,5,7-tetramethylcyclotetrasiloxane, 1.0 part by weight of a platinum-vinylsiloxane complex (SIP6830.3, manufactured by AZmax Co., Ltd.), and 5.0 parts by weight of dicumyl peroxide (Percumyl D, manufactured by NOF Corporation) as a thermal polymerization initiator.

The curable resin composition obtained above was cast to a thickness of 0.4 mm using a roll coater and heated in steps at 80° C. for 1 hour, at 100° C. for 1 hour, at 140° C. for 1 hour, and at 180° C. for 1 hour to yield a molded article in the form of a sheet with a prescribed thickness.

Comparative Example 1

A transparent curable resin composition was obtained by mixing 100 parts by weight of dicyclopentanyl diacrylate (Light Acrylate DCP-A, manufactured by Kyoeisha Chemical Co., Ltd.) and 2.0 parts by weight of 1-hydroxycyclohexyl phenyl ketone (Irgacure 184, manufactured by Ciba Specialty Chemicals) as a photopolymerization initiator.

The curable resin composition obtained above was cast to a thickness of 0.4 mm using a roll coater and cured by irradiating with a high-pressure mercury lamp (output, 30 W/cm) at an integrated exposure dose of 2,000 mJ/cm$^2$ to yield a molded article in the form of a sheet with a prescribed thickness.

[Heat Resistance Test]

The molded articles obtained in the aforementioned Examples 8 to 15 and Comparative Example 1 were respectively tested for the modulus of elasticity, elongation at break, and transmission and, in addition, for the transmission at 400 nm after a heat resistance test (3-hour heating at 230° C.) with the aid of a spectrophotometer. The results are shown in Table 1. The modulus of elasticity and the elongation at break were measured in conformity to the tensile test described in JIS K 7212 (dimension of test piece, 100×25×0.4 mm; distance between chucks, 50 mm; test rate, 5 mm/min) and evaluated on the basis of the mean test value (n=5).

TABLE 1

| | Modulus of elasticity | Elongation at break | Transmission (400 nm) | Transmission after heat resistance test (400 nm) |
|---|---|---|---|---|
| Example 8 | 150 MPa | 15% | 89% | 88% |
| Example 9 | 210 MPa | 14% | 89% | 87% |
| Example 10 | 630 MPa | 14% | 89% | 84% |
| Example 11 | 280 MPa | 13% | 89% | 83% |
| Example 12 | 460 Mpa | 12% | 89% | 83% |
| Example 13 | 1490 MPa | 10% | 89% | 80% |
| Example 14 | 1040 MPa | 12% | 89% | 80% |
| Example 15 | 1310 MPa | 10% | 89% | 81% |
| Comparative Example 1 | 1680 MPa | 5% | 87% | 14% |

As is apparent from Table 1, the molded articles obtained in Examples 8 to 15 are lower in the tensile strength and higher in the elongation at break than the one obtained in Comparative Example 1 and this indicates that the molded articles in the Examples are superior in flexibility to the one in Comparative Example; Furthermore, the transmission of the molded articles obtained in Examples 8 to 15 is superior to that of the molded article obtained in Comparative Example 1 and this is particularly pronounced in the transmission after the heat resistance test.

The invention claimed is:

1. A process for producing a cage-type curable silicone copolymer characterized by having a constituent unit represented by the following general formula (1):

$$Y-[Z-(O_{1/2}-R^2{}_2SiO_{1/2})_a-(R^1SiO_{3/2})_n-(O_{1/2})_b]_m-Z-Y \quad (1)$$

wherein $R^1$ and $R^2$ each is a vinyl group, an alkyl group, a phenyl group, a (meth)acryloyl group, an allyl group, or an oxirane ring-containing group; the substituents selected for $R^1$ and $R^2$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$ and n denotes a number of 8-14; in the case where n is an odd number, a and b are a combination of an even number and an odd number including 0; in the case where n is an even number, a and b are a combination of even numbers including 0; m denotes a number of 1-2,000; Z is a divalent group represented by the following general formula (2)

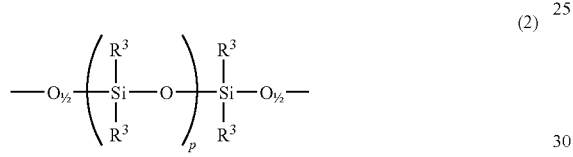

wherein $R^3$ is a hydrogen atom, a vinyl group, an alkyl group, a phenyl group, a (meth)acryloyl group, an allyl group, or an oxirane ring-containing group, the substituents selected for $R^3$ may be identical with or different from one another, and p denotes a number of 0-30; and Y is a monovalent group selected from the following general formulas (3) to (6)

$$[(R^4O)R^2{}_2SiO_{1/2}]_a-[R^1SiO_{3/2}]_n-[O_{1/2}]- \quad (3)$$

$$[R^4O_{1/2}]_b-[R^1SiO_{3/2}]_n-[O_{1/2}-R^2{}_2SiO_{1/2}]- \quad (4)$$

$$(R^4O_{1/2})- \quad (5)$$

$$(R^2{}_3SiO_{1/2})- \quad (6)$$

wherein $R^1$ and $R^2$ each is a vinyl group, an alkyl group, a phenyl group, a (meth)acryloyl group, an allyl group, or an oxirane ring-containing group; the substituents selected for $R^1$ or $R^2$ may be identical with or different from one another; $R^4$ is selected from a hydrogen atom, a methyl group, and an ethyl group; a and b each is a number of 0-3 and n denotes a number of 8-14; in the case where n is an odd number, a and b each is independently 0 or 2; in the case where n is an even number, a and b each is independently 1 or 3: the said process comprising condensing a cage-type siloxane compound containing an alkoxyl group or silanol group represented by the following general formula (7)

$$[(R^4O)R^2{}_2SiO_{1/2}]_a-[R^1SiO_{3/2}]_n-[O_{1/2}R^4]_b \quad (7)$$

wherein $R^1$ and $R^2$ each is selected from a vinyl group, an alkyl group, a phenyl group, a (meth)acryloyl group, an allyl group, and an oxirane ring-containing group; $R^4$ is selected from a hydrogen atom, a methyl group, and an ethyl group; the substituents selected for $R^1$, $R^2$, or $R^4$ may be identical with or different from one another and at least one of the substituents selected for $R^1$ contained in a molecule is a vinyl group, a (meth)acryloyl group, an allyl group, or an oxirane ring-containing group; a and b each is a number of 0-3 and satisfies the relationship $1 \leq a+b \leq 4$; further, n is an integer of 8-14; in the case where n is an odd number, a and b are a combination of an even number and an odd number including 0; in the case where n is an even number, a and b are a combination of even numbers including 0 with a compound represented by the following compound (8)

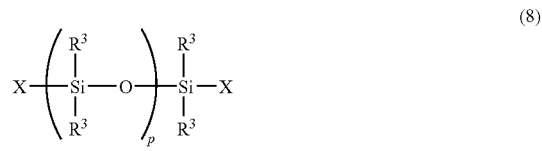

wherein $R^3$ is a hydrogen atom, a vinyl group, an alkyl group, a phenyl group, a (meth)acryloyl group, an allyl group, or an oxirane ring-containing group; the substituents selected for $R^3$ may be identical with or different from one another; X is a hydroxyl group, a hydrogen atom, a chlorine atom, or an alkoxyl group; the substituents selected for X may be identical with or different from one another; further, p denotes a number of 0-30, and then condensing the said condensation reaction product with a compound represented by the following general formula (9)

$$R^2{}_3Si-X \quad (9)$$

wherein $R^2$ is a hydrogen atom, a vinyl group, an alkyl group, a phenyl group, a (meth)acryloyl group, an allyl group, or an oxirane ring-containing group, the substituents selected for $R^2$ may be identical with or different from one another, and X is a hydroxyl group, a hydrogen atom, a chlorine atom, or an alkoxyl group, wherein the process further comprises mixing a cage-type siloxane compound represented by the following general formula (19)

$$[R^1SiO_{3/2}]_n \quad (19)$$

wherein $R^1$ is selected from a vinyl group, an alkyl group, a phenyl group, a (meth)acryloyl group, an allyl group, and an oxirane ring-containing group, the substituents selected for $R^1$ may be identical with or different from one another, and n is an integer of 8-14; with a dialkoxysilane represented by the following general formula (20)

$$R^2{}_2Si(OR^5)_2 \quad (20)$$

wherein $R^2$ is selected from a vinyl group, an alkyl group, a phenyl group, a (meth)acryloyl group, an allyl group, and an oxirane ring-containing group, $R^5$ is selected from a methyl group and an ethyl group, and the substituents selected for $R^2$ or $R^5$ may be identical with or different from one another; at a molar ratio $[R^1SiO_{3/2}]_n$: $R^2{}_2Si(OR^5)_2$ in the range of 1:0.5 to 1:2, and subjecting the mixture to addition reaction in a non-polar solvent in the presence of a basic catalyst to yield a cage-type siloxane compound containing an alkoxyl group represented by general formula (7).

2. A process for producing a curable cage-type silicone copolymer as described in claim 1 wherein 1 mole of a cage-type silsesquioxane compound containing an alkoxyl group or silanol group represented by general formula (7) is subjected to a condensation reaction with 0.5-10 moles of a compound represented by general formula (8).

3. A process for producing a curable cage-type silicone copolymer as described in claim 1 wherein 1 mole of a cage-type silsesquioxane compound containing an alkoxyl group or silanol group represented by general formula (7) is subjected to a condensation reaction with 0.5-10 moles of a compound represented by general formula (8) and with 2-100 moles of a compound represented by general formula (9).

4. A curable resin composition formed by incorporating a hydrosylilation catalyst or a radical initiator or both in the curable cage-type silicone copolymer obtained by the process described in claim 1.

5. A curable resin composition as described in claim 4 wherein a hydrosylilatable compound having a hydrogen atom on at least one silicon atom or a compound having an unsaturated group in the molecule or both are further incorporated.

6. A molded article obtained by curing the curable resin composition described in claim 5.

7. A process for producing a curable cage-type silicone copolymer as described in claim 1 wherein the product cage-type siloxane compound containing an alkoxyl group has a number average molecular weight $M_n$ in the range of 500-2,000 and a molecular weight distribution, weight average molecular weight $M_w$/number average molecular weight $M_n$, in the range of 1.0-2.0.

8. A process for producing a curable cage-type silicone copolymer as described in claim 1, further comprising hydrolyzing the addition product in the presence of an acid catalyst or a basic catalyst to yield a cage-type siloxane compound containing a silanol group represented by general formula (7).

9. A process for producing a curable cage-type silicone copolymer as described in claim 8 wherein the product cage-type siloxane compound containing a silanol group has a number average molecular weight $M_n$ in the range of 500-2,000 and a molecular weight distribution, weight average molecular weight $M_w$/number average molecular weight $M_n$, in the range of 1.0-2.0.

10. A molded article obtained by curing the curable resin composition described in claim 5.

\* \* \* \* \*